United States Patent
Gooding et al.

(10) Patent No.: US 9,642,748 B2
(45) Date of Patent: *May 9, 2017

(54) PATIENT INTERFACE FOR OPHTHALMOLOGIC DIAGNOSTIC AND INTERVENTIONAL PROCEDURES

(71) Applicant: OPTIMEDICA CORPORATION, Sunnyvale, CA (US)

(72) Inventors: Phillip Gooding, Mountain View, CA (US); Michael W. Wiltberger, Santa Clara, CA (US); Christine Beltran, Sunnyvale, CA (US); Jonathan H. Talamo, Newton, MA (US)

(73) Assignee: Optimedica Corporation, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/965,830

(22) Filed: Dec. 10, 2015

(65) Prior Publication Data

US 2016/0095517 A1    Apr. 7, 2016

Related U.S. Application Data

(63) Continuation of application No. 13/279,155, filed on Oct. 21, 2011, now Pat. No. 9,237,967.

(51) Int. Cl.
*A61B 18/18*    (2006.01)
*A61F 9/008*    (2006.01)
(Continued)

(52) U.S. Cl.
CPC ........ *A61F 9/00825* (2013.01); *A61B 3/0008* (2013.01); *A61B 3/0025* (2013.01);
(Continued)

(58) Field of Classification Search
CPC ....... A61B 3/102; A61B 3/0008; A61B 3/107; A61B 3/113; A61B 19/54;
(Continued)

(56) References Cited

U.S. PATENT DOCUMENTS

| 4,838,266 A | 6/1989 | Koziol et al. |
| 4,891,043 A | 1/1990 | Zeimer et al. |

(Continued)

FOREIGN PATENT DOCUMENTS

| DE | 4430720 A1 | 6/1995 |
| DE | 102004025999 A1 | 12/2005 |

(Continued)

OTHER PUBLICATIONS

International Search Report and Written Opinion for Application No. PCT/US2011/050448, mailed on Dec. 9, 2011, 10 pages.

(Continued)

*Primary Examiner* — William Thomson
*Assistant Examiner* — John R Downey
(74) *Attorney, Agent, or Firm* — Abbott Medical Optics Inc.

(57) ABSTRACT

An ophthalmic system may comprise an imaging device having a field of view oriented toward the eye of the patient; a patient interface housing defining a passage therethrough, having a distal end coupled to one or more seals configured to be directly engaged with one or more surfaces of the eye of the patient, and wherein the proximal end is configured to be coupled to the patient workstation such that at least a portion of the field of view of the imaging device passes through the passage; and two or more registration fiducials coupled to the patient interface housing in a predetermined geometric configuration relative to the patient interface housing within the field of view of the imaging device such that they may be imaged by the imaging device in reference (Continued)

to predetermined geometric markers on the eye of the patient which may also be imaged by the imaging device.

27 Claims, 38 Drawing Sheets

(51) Int. Cl.
| | |
|---|---|
| A61B 3/10 | (2006.01) |
| A61F 9/009 | (2006.01) |
| A61B 3/00 | (2006.01) |
| A61B 3/14 | (2006.01) |
| A61B 90/00 | (2016.01) |

(52) U.S. Cl.
CPC ............... *A61B 3/102* (2013.01); *A61B 3/14* (2013.01); *A61B 90/39* (2016.02); *A61F 9/009* (2013.01); *A61F 9/0084* (2013.01); *A61F 9/00817* (2013.01); *A61B 2090/3983* (2016.02); *A61F 2009/0087* (2013.01); *A61F 2009/00851* (2013.01); *A61F 2009/00887* (2013.01); *A61F 2009/00897* (2013.01)

(58) Field of Classification Search
CPC .. A61F 2009/00872; A61F 2009/00844; A61F 2009/00846; A61F 2009/00851
USPC ........................................................ 606/4–6
See application file for complete search history.

(56) References Cited

U.S. PATENT DOCUMENTS

| | | | |
|---|---|---|---|
| 5,336,215 | A | 8/1994 | Hsueh et al. |
| 5,437,658 | A | 8/1995 | Muller et al. |
| 5,507,741 | A | 4/1996 | L'Esperance |
| 5,533,998 | A | 7/1996 | Freese et al. |
| 5,549,632 | A | 8/1996 | Lai |
| 5,620,436 | A | 4/1997 | Lang et al. |
| 5,720,894 | A | 2/1998 | Neev et al. |
| 5,738,677 | A | 4/1998 | Colvard et al. |
| 5,741,245 | A | 4/1998 | Cozean et al. |
| 5,772,675 | A | 6/1998 | Hellenkamp |
| 5,957,915 | A | 9/1999 | Trost |
| 5,984,916 | A | 11/1999 | Lai |
| 6,019,472 | A | 2/2000 | Koester et al. |
| 6,210,399 | B1 | 4/2001 | Parel et al. |
| 6,344,040 | B1 | 2/2002 | Juhasz et al. |
| 6,454,761 | B1 | 9/2002 | Freedman |
| 6,863,667 | B2 | 3/2005 | Webb et al. |
| 7,125,119 | B2 | 10/2006 | Farberov |
| 7,146,983 | B1 | 12/2006 | Hohla et al. |
| 7,390,089 | B2 | 6/2008 | Loesel et al. |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,394,084 | B2 | 3/2013 | Blumenkranz et al. |
| 8,414,564 | B2 | 4/2013 | Goldshleger et al. |
| 8,475,433 | B2 | 7/2013 | Mrochen et al. |
| 8,500,723 | B2 | 8/2013 | Frey et al. |
| 8,506,559 | B2 | 8/2013 | Raksi |
| 8,518,026 | B2 | 8/2013 | Culbertson et al. |
| 8,556,425 | B2 | 10/2013 | Frey et al. |
| 8,623,001 | B2 | 1/2014 | Preuss et al. |
| 8,753,321 | B2 | 6/2014 | Mrochen et al. |
| 8,845,624 | B2 | 9/2014 | Raksi et al. |
| 8,968,375 | B2 | 3/2015 | Culbertson et al. |
| 9,044,302 | B2 | 6/2015 | Gooding et al. |
| 9,233,023 | B2 | 1/2016 | Culbertson et al. |
| 2003/0158543 | A1 | 8/2003 | Van Saarloos et al. |
| 2004/0179167 | A1 | 9/2004 | Dahi et al. |
| 2004/0225284 | A1 | 11/2004 | Webb et al. |
| 2005/0054900 | A1 | 3/2005 | Mawn et al. |
| 2006/0195078 | A1 | 8/2006 | Webb et al. |
| 2007/0010803 | A1 | 1/2007 | Bischoff et al. |
| 2007/0093795 | A1 | 4/2007 | Melcher et al. |
| 2007/0093796 | A1 | 4/2007 | Raksi et al. |
| 2007/0173791 | A1 | 7/2007 | Raksi |
| 2007/0177103 | A1 | 8/2007 | Migliaccio et al. |
| 2007/0189664 | A1 | 8/2007 | Andersen et al. |
| 2007/0225691 | A1 | 9/2007 | Silvestrini et al. |
| 2008/0071254 | A1 | 3/2008 | Lummis et al. |
| 2008/0103367 | A1 | 5/2008 | Burba et al. |
| 2008/0242978 | A1 | 10/2008 | Simon et al. |
| 2008/0243107 | A1 | 10/2008 | Muhlhoff et al. |
| 2008/0262390 | A1 | 10/2008 | Bangera et al. |
| 2009/0012507 | A1 | 1/2009 | Culbertson et al. |
| 2009/0069794 | A1 | 3/2009 | Kurtz |
| 2009/0182311 | A1 | 7/2009 | Gertner et al. |
| 2009/0211586 | A1 | 8/2009 | Shea et al. |
| 2010/0179418 | A1 | 7/2010 | Mueller et al. |
| 2010/0191226 | A1 | 7/2010 | Blumenkranz et al. |
| 2010/0256614 | A1 | 10/2010 | Donitzky et al. |
| 2010/0324543 | A1 | 12/2010 | Kurtz et al. |
| 2011/0022035 | A1 | 1/2011 | Porter et al. |
| 2011/0172649 | A1 | 7/2011 | Schuele et al. |
| 2011/0184395 | A1 | 7/2011 | Schuele et al. |
| 2011/0190740 | A1 | 8/2011 | Frey et al. |
| 2011/0190741 | A1 | 8/2011 | Deisinger et al. |
| 2011/0196350 | A1 | 8/2011 | Friedman et al. |
| 2011/0202046 | A1 | 8/2011 | Angeley et al. |
| 2011/0319875 | A1 | 12/2011 | Loesel et al. |
| 2012/0016349 | A1 | 1/2012 | Brownell |
| 2012/0143050 | A1 | 6/2012 | Heigl |
| 2013/0035672 | A1 | 2/2013 | Raksi |
| 2013/0035674 | A1 | 2/2013 | Lummis et al. |
| 2013/0053837 | A1 | 2/2013 | Kandulla et al. |
| 2014/0341451 | A1 | 11/2014 | Angeley et al. |

FOREIGN PATENT DOCUMENTS

| | | |
|---|---|---|
| DE | 102007020565 A1 | 10/2008 |
| EP | 1034755 A1 | 9/2000 |
| EP | 1970034 A1 | 9/2008 |
| EP | 2057973 A1 | 5/2009 |
| RU | 2008787 C1 | 3/1994 |
| WO | 8705496 A1 | 9/1987 |
| WO | 2005039462 A1 | 5/2005 |
| WO | 2008110368 A1 | 9/2008 |
| WO | 2010022745 A1 | 3/2010 |
| WO | 2011023232 A1 | 3/2011 |
| WO | 2011163507 A2 | 12/2011 |

OTHER PUBLICATIONS

International Search Report and Written Opinion for Application No. PCT/US2012/061187, mailed on Mar. 25, 2013, 11 pages.
Supplementary Partial European Search Report for European Application No. EP12841512, mailed on Jun. 20, 2016, 7 pages.
Supplementary European Search Report for European Application No. EP12841512, mailed on Oct. 21, 2016, 12 pages.

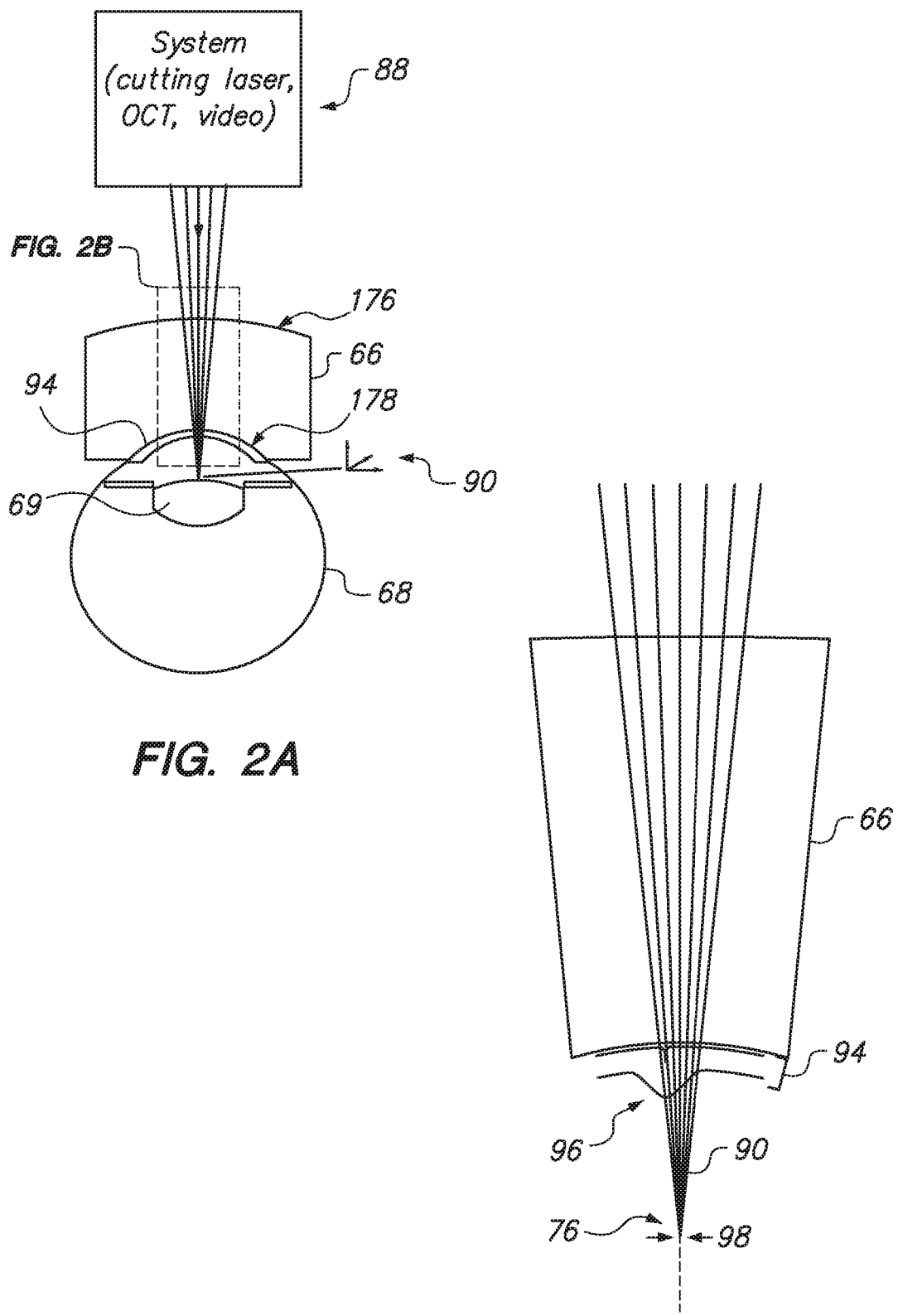

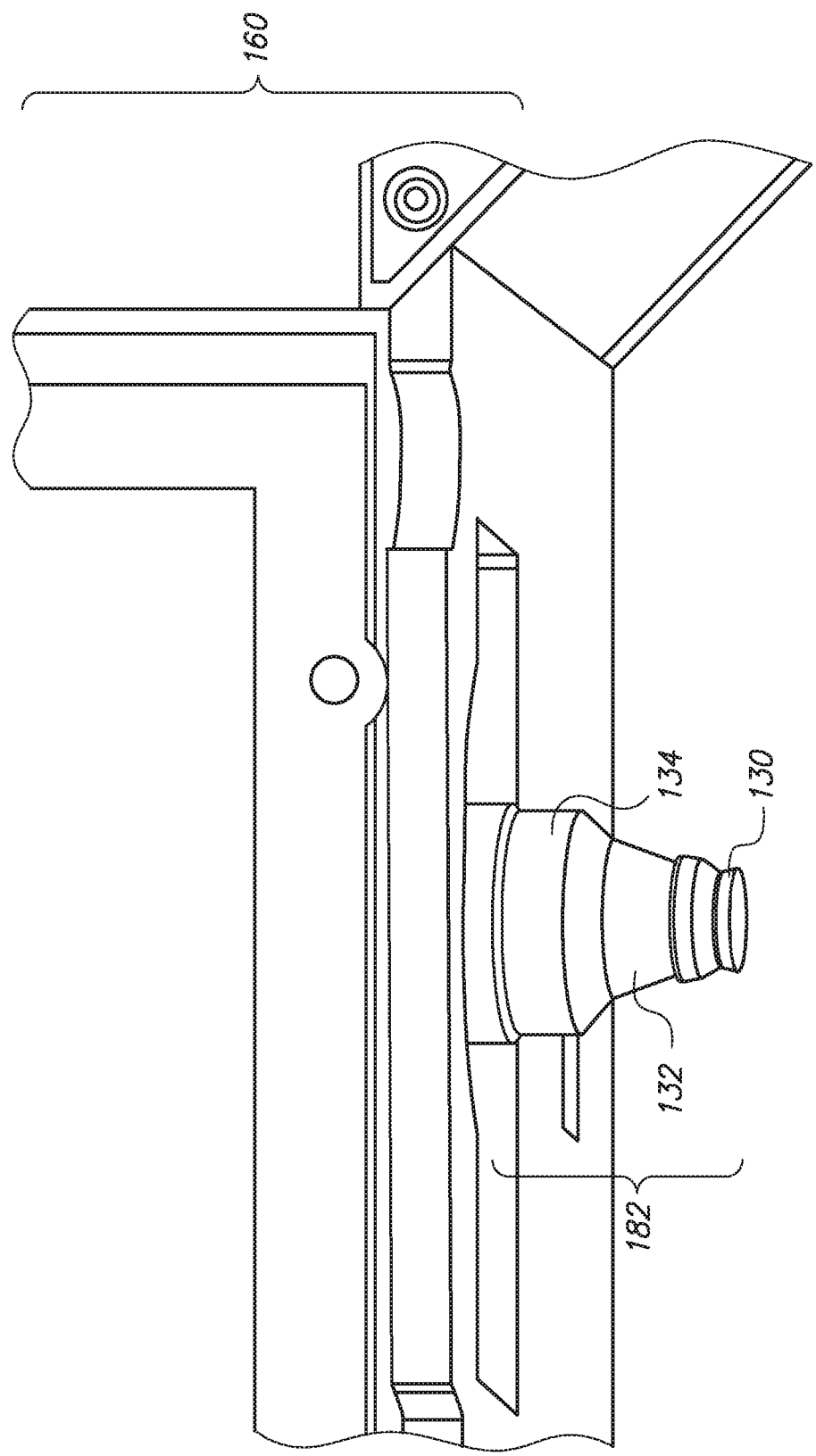

PATIENT INTERFACE FOR OPHTHALMOLOGIC DIAGNOSTIC AND INTERVENTIONAL PROCEDURES

This application claims priority to and is a continuation of U.S. patent application Ser. No. 13/279,155, filed Oct. 21, 2011, which is incorporated herein in its entirety by reference.

FIELD OF THE INVENTION

The present invention relates to ophthalmic surgical procedures and systems.

BACKGROUND

Cataract extraction is one of the most commonly performed surgical procedures in the world with approximately 4 million cases performed annually in the United States and 15 million cases worldwide. This market is composed of various segments including intraocular lenses for implantation, viscoelastic polymers to facilitate surgical maneuvers, disposable instrumentation including ultrasonic phacoemulsification tips, tubing, and various knives and forceps. Modern cataract surgery is typically performed using a technique termed "phacoemulsification" in which an ultrasonic tip with an associated water stream for cooling purposes is used to sculpt the relatively hard nucleus of the lens after creation of an opening in the anterior lens capsule termed "anterior capsulotomy" or more recently "capsulorhexis". Following these steps as well as removal of residual softer lens cortex by aspiration methods without fragmentation, a synthetic foldable intraocular lens, or "IOL", may be inserted into the eye through a small incision.

One of the earliest and most critical steps in the procedure is the creation, or performance, of capsulorhexis. This step evolved from an earlier technique termed "can-opener capsulotomy" in which a sharp needle was used to perforate the anterior lens capsule in a circular fashion followed by the removal of a circular fragment of lens capsule typically in the range of 5-8 mm in diameter. This facilitated the next step of nuclear sculpting by phacoemulsification. Due to a variety of complications associated with variations of the can-opener technique, attempts were made by leading experts in the field to develop a better technique for removal of the anterior lens capsule preceding the emulsification step. The concept of the capsulorhexis is to provide a smooth continuous circular opening through which not only the phacoemulsification of the nucleus can be performed safely and easily, but also for easy insertion of the intraocular lens. It provides both a clear central access for insertion, a permanent aperture for transmission of the image to the retina by the patient, and also a support of the IOL inside the remaining capsule that would limit the potential for dislocation.

More modern techniques, such as those employing lasers to assist with the creation of precision capsulorhexis geometries as well as other desired incisions, such as tissue structure relaxing incisions of various types, are disclosed, for example, in U.S. patent application Ser. Nos. 11/328,970, 12/510,148, 12/048,182, 12/048,185, 12/702,242, 12/048,186, 61/289,837, 61/293,357, 61/297,624, and 61/302,437, each of which is incorporated by reference herein in its entirety. Each of these technologies generally requires a patient interface—a structure to join the patient's eye and the laser and associated imaging systems, and to optimize the interaction between the diagnostic and imaging technologies and the pertinent patient tissue structures. There is a need for further optimization of the patient interface options to advance the standard of care of the cataract patient.

BRIEF DESCRIPTION OF THE DRAWINGS

FIGS. 2A-2C illustrate aspects of patient interface configurations featuring a focusing lens engaged adjacent a cornea of a patient.

FIGS. 3A-3C illustrate aspects of one-piece patient interface embodiments.

SUMMARY OF THE INVENTION

Figure 1:
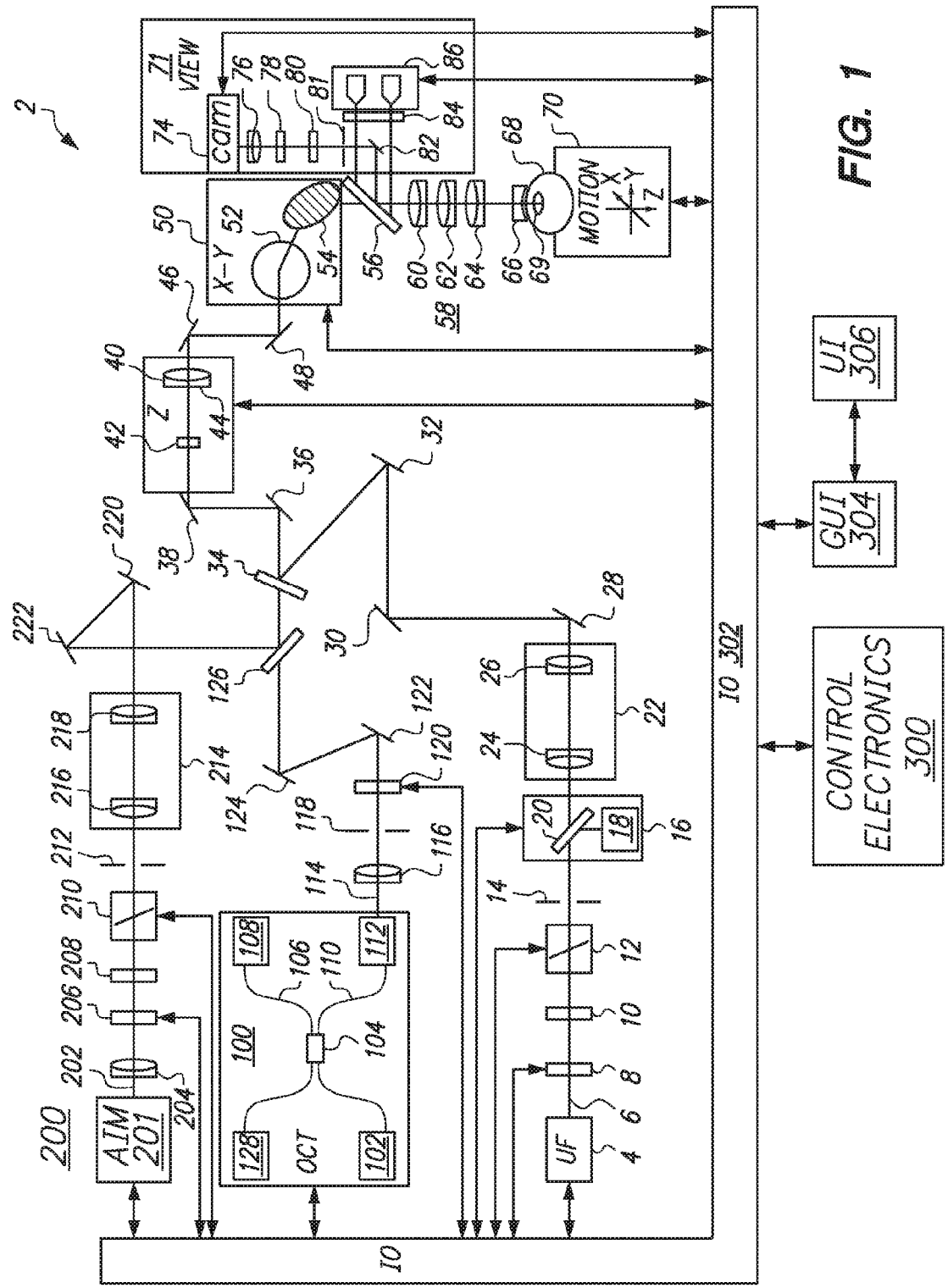
FIG. 1 illustrates one embodiment of a diagnostic/interventional ophthalmic system.

One embodiment is directed to a system for ophthalmic intervention on an eye of a patient, comprising: an imaging device having a field of view oriented toward the eye of the patient; a patient interface housing having proximal and distal ends and defining a passage therethrough, wherein the distal end is coupled to one or more seals configured to be directly engaged with one or more surfaces of the eye of the patient, and wherein the proximal end is configured to be coupled to the patient workstation such that at least a portion of the field of view of the imaging device passes through the passage; and two or more registration fiducials coupled to the patient interface housing in a predetermined geometric configuration relative to the patient interface housing within the field of view of the imaging device such that they may be imaged by the imaging device in reference to predetermined geometric markers on the eye of the patient which may also be imaged by the imaging device. The system may further comprise a laser system operatively coupled to the imaging device. The laser system may be configured to produce a treatment beam that may be directed through the passage of the patient interface housing and into the eye of the patient. The treatment beam may be suitable for creating dielectric breakdown within a cataractous crystalline lens of the eye. The laser system may be configured to produce a pulsed treatment beam with a pulse repetition rate between about 1 kHz and about 200 kHz. The laser system may be configured to produce a treatment beam having a wavelength between about 800 nm and about 1,100 nm. The laser system may be configured to produce a pulsed treatment beam having a pulse energy between about 1 microjoule and about 1,000 microjoules. The laser system may be configured to produce a pulsed treatment beam with a pulse duration between about 100 femtoseconds and about 10 picoseconds. The system may further comprise an optical lens coupled to the housing and having a focal axis aligned to pass through the passage of the housing. The system may further comprise an illumination source configured to direct illumination radiation from a position adjacent the imaging device toward the eye of the patient. The illumination source may be configured to direct at least a portion of the illumination radiation through the passage of the patient interface housing. At least a portion of the patient interface housing may be at least partially translucent to the illumination radiation, and wherein the illumination source is configured to direct at least a portion of the illumination radiation across the translucent portion of the patient interface housing toward the eye of the patient. The illumination radiation may be infrared radiation. The illumination radiation may be visible light radiation. The imaging device may comprise an optical coherence tomography system configured to measure the coherence of radiation scattered into an interferometer from the field of view. The fiducials comprise one or more materials that fluoresce in infrared radiation. The fiducials may comprise one or more materials that highly contrast in infrared radiation relative to other surrounding materials. The fiducials may comprise one or more surface irregularities relative to other surrounding surfaces. The one or more surface irregularities may be selected from the group consisting of: a concave feature, a convex feature, a depressed edge, a depressed step, a projecting edge, a projecting step, and an intersection of lines. The fiducials may comprise one or more materials that highly contrast in visible light radiation relative to other surrounding materials. The fiducials may comprise one or more surface irregularities relative to other surrounding surfaces. The one or more surface irregularities may be selected from the group consisting of: a concave feature, a convex feature, a depressed edge, a depressed step, a projecting edge, a projecting step, and an intersection of lines. The fiducials may comprise one or more surface irregularities relative to other surrounding surfaces. The one or more surface irregularities may be selected from the group consisting of: a concave feature, a convex feature, a depressed edge, a depressed step, a projecting edge, a projecting step, and an intersection of lines. The two or more fiducials may be positioned upon an inner annulus formed by the distal end of the patient interface housing. The two or more fiducials may comprise two fiducials positioned at opposite sides of the inner annulus. The two or more fiducials may comprise three fiducials distributed nonhomogeneously about the inner annulus.

DETAILED DESCRIPTION

As described briefly above, one embodiment of a cataract diagnostic and interventional system may be implemented by a system that projects or scans an optical beam into a patient's eye (68), such as system (2) shown in FIG. 1 which includes an ultrafast ("UF") light source or treatment beam 4 (e.g. a femtosecond laser suitable for creating dielectric breakdown within a cataractous crystalline lens of an eye). Using this system, a treatment beam may be scanned through a patient interface and into a patient's eye in three dimensions: X, Y, Z. In this embodiment, the UF wavelength can vary between about 800 nm and about 1100 nm and the pulse width can vary from about 100 fs to about 10 picoseconds. The pulse energy of a suitable pulsed treatment beam may have a pulse energy of between about 1 microjoule and about 1,000 microjoules. The pulse repetition frequency can also vary from about 1 kHz to about 250 kHz. Safety limits with regard to unintended damage to non-targeted tissue bound the upper limit with regard to repetition rate and pulse energy; while threshold energy, time to complete the procedure and stability bound the lower limit for pulse energy and repetition rate. The peak power of the focused spot in the eye (68) and specifically within the crystalline lens (69) and anterior capsule of the eye is sufficient to produce optical breakdown and initiate a plasma-mediated ablation process. Near-infrared wavelengths are preferred because linear optical absorption and scattering in biological tissue is reduced across that spectral range. As an example, laser (4) may be a repetitively pulsed 1035 nm device that produces 500 fs pulses at a repetition rate of 100 kHz and an individual pulse energy in the ten microjoule range.

The laser (4) is controlled by control electronics (300), via an input and output device (302), to create optical beam (6). Control electronics (300) may be a computer, microcontroller, etc. In this example, the entire system is controlled by the controller (300), and data moved through input/output device IO (302). A graphical user interface GUI (304) may be used to set system operating parameters, process user input (UI) (306) on the GUI (304), and display gathered information such as images of ocular structures.

The generated UF light beam (6) proceeds towards the patient eye (68) passing through half-wave plate, (8), and linear polarizer, (10). The polarization state of the beam can be adjusted so that the desired amount of light passes through half-wave plate (8) and linear polarizer (10), which together act as a variable attenuator for the UF beam (6). Additionally, the orientation of linear polarizer (10) determines the incident polarization state incident upon beamcombiner (34), thereby optimizing beamcombiner throughput.

The UF beam proceeds through a shutter (12), aperture (14), and a pickoff device (16). The system controlled shutter (12) ensures on/off control of the laser for procedural and safety reasons. The aperture sets an outer useful diameter for the laser beam and the pickoff monitors the output of the useful beam. The pickoff device (16) includes of a partially reflecting mirror (20) and a detector (18). Pulse energy, average power, or a combination may be measured using detector (18). The information can be used for feedback to the half-wave plate (8) for attenuation and to verify whether the shutter (12) is open or closed. In addition, the shutter (12) may have position sensors to provide a redundant state detection.

The beam passes through a beam conditioning stage (22), in which beam parameters such as beam diameter, divergence, circularity, and astigmatism can be modified. In this illustrative example, the beam conditioning stage (22) includes a 2 element beam expanding telescope comprised of spherical optics (24) and (26) in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the optical system (22) can be used to image aperture (14) to a desired location (e.g. the center location between the 2-axis scanning device 50 described below). In this way, the amount of light that makes it through the aperture (14) is assured to make it through the scanning system. Pickoff device (16) is then a reliable measure of the usable light.

After exiting conditioning stage (22), beam (6) reflects off of fold mirrors (28, 30, & 32). These mirrors can be adjustable for alignment purposes. The beam (6) is then incident upon beam combiner (34). Beamcombiner (34) reflects the UF beam (6) (and transmits both the OCT 114 and aim 202 beams described below). For efficient beamcombiner operation, the angle of incidence is preferably kept below 45 degrees and the polarization where possible of the beams is fixed. For the UF beam (6), the orientation of linear polarizer (10) provides fixed polarization.

Following the beam combiner (34), the beam (6) continues onto the z-adjust or Z scan device (40). In this illustrative example the z-adjust includes a Galilean telescope with two lens groups (42 and 44) (each lens group includes one or more lenses). Lens group (42) moves along the z-axis about the collimation position of the telescope. In this way, the focus position of the spot in the patient's eye (68) moves along the z-axis as indicated. In general there is a fixed linear relationship between the motion of lens (42) and the motion of the focus. In this case, the z-adjust telescope has an approximate 2.times.beam expansion ratio and a 1:1 relationship of the movement of lens (42) to the movement of the focus. Alternatively, lens group (44) could be moved along the z-axis to actuate the z-adjust, and scan. The z-adjust is the z-scan device for treatment in the eye (68). It can be controlled automatically and dynamically by the system and selected to be independent or to interplay with the X-Y scan device described next. Mirrors (36 and 38) can be used for aligning the optical axis with the axis of z-adjust device (40). After passing through the z-adjust device (40), the beam (6) is directed to the x-y scan device by mirrors (46 & 48). Mirrors (46 & 48) can be adjustable for alignment purposes. X-Y scanning is achieved by the scanning device (50) preferably using two mirrors (52 & 54) under the control of control electronics (300), which rotate in orthogonal directions using motors, galvanometers, or any other well known optic moving device. Mirrors (52 & 54) are located near the telecentric position of the objective lens (58) and focussing lens (66) combination described below. Tilting these mirrors (52/54) causes them to deflect beam (6), causing lateral displacements in the plane of UF focus located in the patient's eye (68). Objective lens (58) may be a complex multi-element lens element, as shown, and represented by lenses (60, 62, and 64). The complexity of the lens (58) will be dictated by the scan field size, the focused spot size, the available working distance on both the proximal and distal sides of objective 58, as well as the amount of aberration control. An f-theta lens 58 of focal length 60 mm generating a spot size of 10 .mu.m, over a field of 10 mm, with an input beam size of 15 mm diameter is an example. Alternatively, X-Y scanning by scanner (50) may be achieved by using one or more moveable optical elements (e.g. lenses, gratings) which also may be controlled by control electronics (300), via input and output device (302).

The aiming and treatment scan patterns can be automatically generated by the scanner (50) under the control of controller (300). Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional focussing lens (66), which also may be loosely termed a "contact lens", which can be any suitable ophthalmic lens, can be used to help further focus the optical beam (6) into the patient's eye (68) while helping to stabilize eye position. The positioning and character of optical beam 6 and/or the scan pattern the beam 6 forms on the eye (68) may be further controlled by use of an input device such as a joystick, or any other appropriate user input device (e.g. GUI 304) to position the patient and/or the optical system.

The UF laser (4) and controller (300) can be set to target the surfaces of the targeted structures in the eye (68) and ensure that the beam (6) will be focused where appropriate and not unintentionally damage non-targeted tissue. Imaging modalities and techniques described herein, such as for example, Optical Coherence Tomography ("OCT"), Purkinje imaging, Scheimpflug imaging, confocal or non-linear optical microscopy, fluorescence imaging, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography, Purkinje imaging, Scheimpflug imaging, confocal or nonlinear optical microscopy, fluorescence imaging, ultrasound, or other known ophthalmic or medical imaging modalities and/or combinations thereof. In the embodiment of FIG. 1, an OCT device (100) is described, although other modalities are within the scope of the present invention. Preferably the OCT imaging device will be configured to measure the coherence of radiation scattered into an interferometer from structures within the "field of view" of the associated beam as it is scanned. An OCT scan of the eye will provide information about the axial location of the anterior and posterior lens capsule, the boundaries of the cataract nucleus, as well as the depth of the anterior chamber. This information is then be loaded into the control electronics (300), and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device (100) in FIG. 1 includes a broadband or a swept light source (102) that is split by a fiber coupler (104) into a reference arm (106) and a sample arm (110). The reference arm (106) includes a module (108) containing a reference reflection along with suitable dispersion and path length compensation. The sample arm (110) of the OCT device (100) has an output connector (112) that serves as an interface to the rest of the UF laser system. The return signals from both the reference and sample arms (106, 110) are then directed by coupler (104) to a detection device (128), which employs either time domain, frequency or single point detection techniques. In FIG. 1, a frequency domain technique is used with an OCT wavelength of 920 nm and bandwidth of 100 nm. Exiting connector (112), the OCT beam (114) is collimated using lens (116). The size of the collimated beam (114) is determined by the focal length of lens (116). The size of the beam (114) is dictated by the desired NA at the focus in the eye and the magnification of the beam train leading to the eye (68). Generally, OCT beam (114) does not require as high an NA as the UF beam (6) in the focal plane and therefore the OCT beam (114) is smaller in diameter than the UF beam (6) at the beamcombiner (34) location. Following collimating lens (116) is aperture (118) which further modifies the resultant NA of the OCT beam (114) at the eye. The diameter of aperture (118) is chosen to optimize OCT light incident on the target tissue and the strength of the return signal. Polarization control element (120), which may be active or dynamic, is used to compensate for polarization state changes which may be induced by individual differences in corneal birefringence, for example. Mirrors (122 & 124) are then used to direct the OCT beam 114 towards beamcombiners (126 & 34). Mirrors (122 & 124) may be adjustable for alignment purposes and in particular for overlaying of OCT beam (114) to UF beam (6) subsequent to beamcombiner (34). Similarly, beamcombiner (126) is used to combine the OCT beam (114) with the aim beam (202) described below. Once combined with the UF beam (6) subsequent to beamcombiner (34), OCT beam (114) follows the same path as UF beam (6) through the rest of the system. In this way, OCT beam (114) is indicative of the location of UF beam (6). OCT beam (114) passes through the z-scan 40 and x-y scan (50) devices then the objective lens (58), focussing lens (66) and on into the eye (68). Reflections and scatter off of structures within the eye provide return beams that retrace back through the optical system, into connector (112), through coupler (104), and to OCT detector (128). These return back reflections provide the OCT signals that are in turn interpreted by the system as to the location in X, Y, Z of UF beam (6) focal location.

OCT device (100) works on the principle of measuring differences in optical path length between its reference and sample arms. Therefore, passing the OCT through z-adjust 40 does not extend the z-range of OCT system (100) because the optical path length does not change as a function of movement of 42. OCT system (100) has an inherent z-range that is related to the detection scheme, and in the case of frequency domain detection it is specifically related to the spectrometer and the optical bandwidth of the light source. In the case of OCT system (100) used in FIG. 1, the z-range is approximately 3-5 mm in an aqueous environment. Passing the OCT beam (114) in the sample arm through the z-scan of z-adjust (40) allows for optimization of the OCT signal strength. This is accomplished by focusing the OCT beam (114) onto the targeted structure while accommodating the extended optical path length by commensurately increasing the path within the reference arm (106) of OCT system (100).

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y Z should be conducted in order to match the OCT signal information to the UF focus location and also to the relate to absolute dimensional quantities.

Observation of an aim beam may also be used to assist the user to directing the UF laser focus. Additionally, an aim beam visible to the unaided eye in lieu of the infrared OCT and UF beams can be helpful with alignment provided the aim beam accurately represents the infrared beam parameters. An aim subsystem (200) is employed in the configuration shown in FIG. 1. The aim beam (202) is generated by an aim beam light source (201), such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example. Once the aim beam light source generates aim beam (202), the aim beam (202) is collimated using lens (204). The size of the collimated beam is determined by the focal length of lens (204). The size of the aim beam (202) is dictated by the desired NA at the focus in the eye and the magnification of the beam train leading to the eye (68). Generally, aim beam (202) should have close to the same NA as UF beam (6) in the focal plane and therefore aim beam (202) is of similar diameter to the UF beam at the beamcombiner (34) location. Because the aim beam is meant to stand-in for the UF beam (6) during system alignment to the target tissue of the eye, much of the aim path mimics the UF path as described previously. The aim beam (202) proceeds through a half-wave plate (206) and linear polarizer (208). The polarization state of the aim beam (202) can be adjusted so that the desired amount of light passes through polarizer (208). Elements 206 & 208 therefore act as a variable attenuator for the aim beam (202). Additionally, the orientation of polarizer (208) determines the incident polarization state incident upon beamcombiners (126 and 34), thereby fixing the polarization state and allowing for optimization of the beamcombiners' throughput. Of course, if a semiconductor laser is used as aim beam light source (200), the drive current can be varied to adjust the optical power. The aim beam (202) proceeds through a shutter (210) and aperture (212). The system controlled shutter (210) provides on/off control of the aim beam (202). The aperture (212) sets an outer useful diameter for the aim beam (202) and can be adjusted appropriately. A calibration procedure measuring the output of the aim beam (202) at the eye can be used to set the attenuation of aim beam (202) via control of polarizer (206). The aim beam (202) next passes through a beam conditioning device (214). Beam parameters such as beam diameter, divergence, circularity, and astigmatism can be modified using one or more well known beaming conditioning optical elements. In the case of an aim beam (202) emerging from an optical fiber, the beam conditioning device (214) can simply include a beam expanding telescope with two optical elements (216 and 218) in order to achieve the intended beam size and collimation. The final factors used to determine the aim beam parameters such as degree of collimation are dictated by what is necessary to match the UF beam (6) and aim beam (202) at the location of the eye (68). Chromatic differences can be taken into account by appropriate adjustments of beam conditioning device (214). In addition, the optical system (214) is used to image aperture (212) to a desired location such as a conjugate location of aperture (14). The aim beam (202) next reflects off of fold mirrors (222 & 220), which are preferably adjustable for alignment registration to UF beam (6) subsequent to beam combiner (34). The aim beam (202) is then incident upon beam combiner (126) where the aim beam (202) is combined with OCT beam (114). Beamcombiner (126) reflects the aim beam (202) and transmits the OCT beam (114), which allows for efficient operation of the beamcombining functions at both wavelength ranges. Alternatively, the transmit and reflect functions of beamcombiner (126) can be reversed and the configuration inverted. Subsequent to beamcombiner (126), aim beam (202) along with OCT beam (114) is combined with UF beam (6) by beamcombiner (34).

A device for imaging the target tissue on or within the eye (68) is shown schematically in FIG. 1 as imaging system (71). Imaging system includes an image capture device such as a camera (74) and an illumination light source (86) for creating an image of the target tissue. The imaging system (71) gathers images which may be used by the system controller (300) for providing pattern centering about or within a predefined structure. The illumination light source (86) for the viewing is generally broadband and incoherent. For example, light source (86) can include multiple LEDs as shown. The wavelength of the viewing light source (86) is preferably in the range of 700 nm to 750 nm, but can be anything which is accommodated by the beamcombiner (56), which combines the viewing light with the beam path for UF beam (6) and aim beam (202) (beamcombiner 56 reflects the viewing wavelengths while transmitting the OCT and UF wavelengths). Further details regarding positioning and wavelengths of illumination sources are described below in reference to FIG. 12. The beamcombiner (56) may partially transmit the aim wavelength so that the aim beam (202) can be visible to the viewing camera (74). Optional polarization element (84) in front of light source (86) can be a linear polarizer, a quarter wave plate, a half-wave plate or any combination, and is used to optimize signal. A false color image as generated by the near infrared wavelength is acceptable. The illumination light from light source (86) is directed down towards the eye using the same objective lens (58) and focussing lens (66) as the UF and aim beam (6, 202). The light reflected and scattered off of various structures in the eye (68) are collected by the same lenses (58 & 66) and directed back towards beamcombiner (56). There, the return light is directed back into the viewing path via beam combiner and mirror (82), and on to camera (74). Camera (74) can be, for example but not limited to, any silicon based detector array of the appropriately sized format. Video lens (76) forms an image onto the camera's detector array while optical elements (80 & 78) provide polarization control and wavelength filtering respectively. Aperture or iris (81) provides control of imaging NA and therefore depth of focus and depth of field. A small aperture provides the advantage of large depth of field which aids in the patient docking procedure. Alternatively, the illumination and camera paths can be switched. Furthermore, aim light source (200) can be made to emit in the infrared which would not directly visible, but could be captured and displayed using imaging system (71). Coarse adjust registration is usually needed so that when the focussing lens (66) comes into contact with the cornea and/or sclera, the targeted structures are in the capture range of the X, Y scan of the system. Therefore a docking procedure is preferred, which preferably takes in account patient motion as the system approaches the contact condition (i.e. contact between the patient's eye (68) and the focussing lens (66). The viewing system (71) is configured so that the depth of focus is large enough such that the patient's eye (68) and other salient features may be seen before the focussing lens (66) makes contact with eye (68). Preferably, a motion control system (70) is integrated into the overall control system (2), and may move the patient, the system (2) or elements thereof, or both, to achieve accurate and reliable contact between the focussing, or "contact", lens (66), the housing thereof, and/or the eye (68). In one embodiment, the motion control system (70) may comprise one or more motors responsive to control inputs from a master input device such as a joystick, button set, or computer user interface, to allow an operator to command movements of the motion control system (70) to electromechanically reposition the system relative to the eye of the patient, who will typically be resting substantially horizontally on an adjustable operating table or chair. In another embodiment, the chair or table may have one or more controllably movable aspects, such as an electromechanically movable headrest responsive to inputs at an input device such as a joystick, button set, or computer user interface, which may be configured to assist with maneuvering a patient's head and eye relative to the system (the patient's head may be temporarily coupled to the headrest using a device such as a strap or brace placed around at least a portion of the patient's head). In another embodiment, movement of the motion control system (70) or associated patient chair or table may be manually enabled, preferably with controllable braking configurations at the movable joints to prevent movement in a "locked" configuration. Furthermore, as described below, vacuum suction subsystem and flange may be incorporated into the system and used to stabilize the interfacing between the focusing lens (66), pertinent housing thereof, and the eye (68). In one embodiment the physical alignment of the eye (68) relative to other portions of the system (2) via the focussing lens (66) may be accomplished while monitoring the output of the imaging system (71), and performed manually or automatically by analyzing the images produced by imaging system (71) electronically by means of control electronics (300) via IO (302). Force and/or pressure sensor feedback may also be used to discern contact, as well as to initiate the vacuum subsystem.

FIG. 2A depicts one embodiment of a focussing lens (66) configuration wherein the distal aspect (178) of the lens (66) is placed into direct contact with the cornea and/or sclera (94) of the eye. The scanned beam (90) exiting the system (88) crosses the proximal surface (176) of the lens (66), passes through the lens (66), exits across the distal surface (178) of the lens (66), crosses the cornea and/or sclera (94), and eventually reaches the crystalline lens (69) to facilitate interventional steps such as capsulorhexis. A close-up view is illustrated in FIG. 2B, to demonstrate the notion of undesirable corneal folds (96), which may be associated with excess applanation loads placed upon the cornea with contact lens (66) configurations having a relatively large radii of curvature relative to that of the cornea (in such cases, relatively large applanation loads may be applied to ensure surface contact between the lens 66 and the relatively convex shape of the cornea and/or sclera 94). We have found that corneal folds (96) can degrade the optical path to the interior of the eye, reducing the reliability of laser interaction with the tissue of the eye. Further, it is also generally desirable to minimize intraocular pressure during diagnostic and interventional procedures, and large applanation loads tend to increase intraocular pressure. As a result, in the embodiments depicted in FIGS. 3A-3C and 4A-4E, comprise focusing lenses (66) with distal surface radii of curvature that are substantially close to that of the typical human cornea, thus substantially mitigating applanation and/or interfacing loads, as described in further detail below.

Figure 2C:
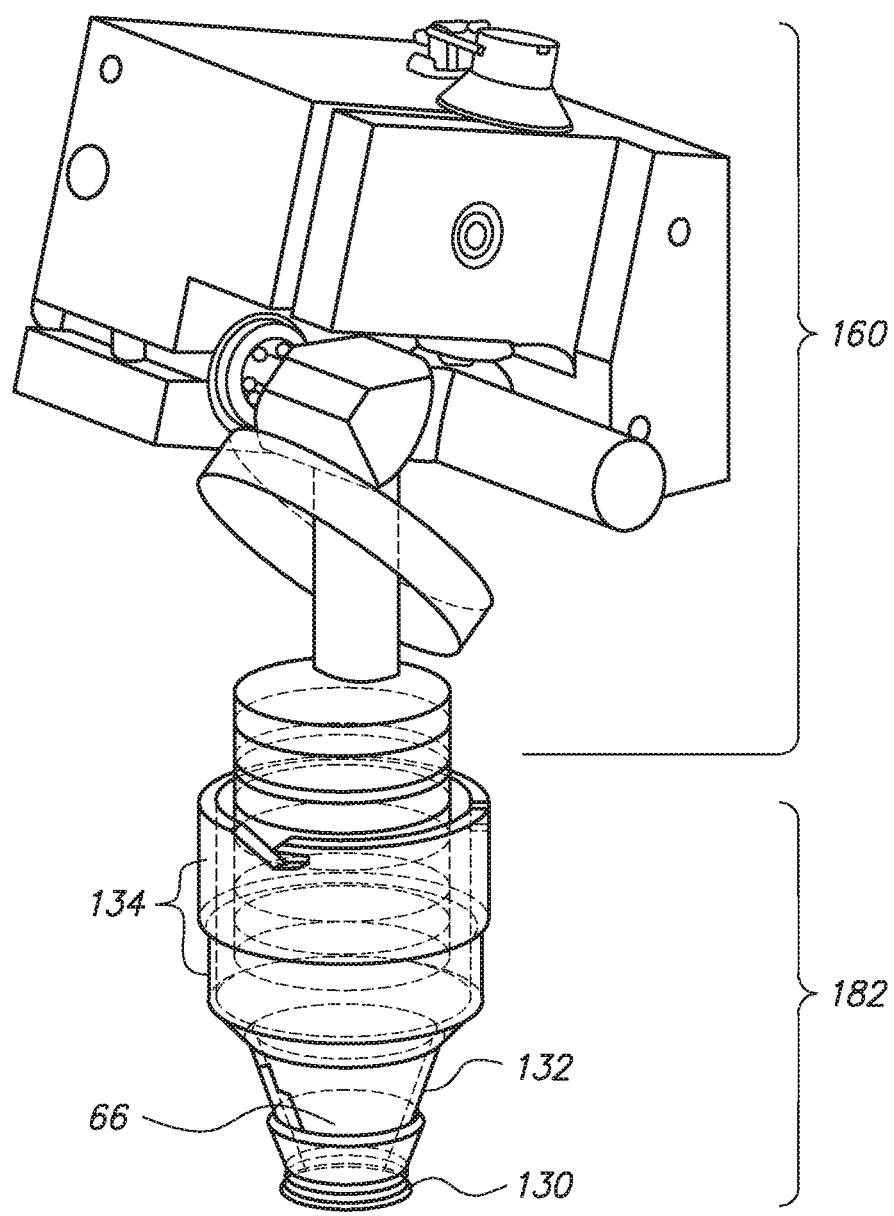

Referring to FIG. 2C, one embodiment of a patient interface (182), which may be referred to as a "one-piece" interface, is shown interfaced with a movable portion (160) of a diagnostic and interventional system such as that described in reference to FIG. 1, the patient interface (182) comprising an interfacial seal configuration (130), a conical lower housing portion (132) which houses a focusing lens (66), and a cylindrical upper housing portion (134) with a proximal aspect configured to mechanically interface and couple with the movable portion (160) of the diagnostic and interventional system. Preferably, in the depicted embodiment and other illustrative embodiments that follow, the patient interface (182) is coupled to the movable portion (160) of the diagnostic and interventional system with a load sensing interface, such as a platform comprising one or more load cells or load sensors (such as MEMS load sensors available from Honeywell, Inc.) configured to provide the operator with output signals or feedback regarding loads being applied at such interface due to coupling with the eye of the patient (i.e., such loads may be monitored since they are representative of contact loads applied to the eye of the patient by the patient interface assembly 182). This feedback may be presented to the user on GUI (304) by control electronics (300) via IO (302). The presentation is intended for the user to interpret in adjusting the directionality of motion control electronics (70) during patient coupling to the system.

Figure 3B:
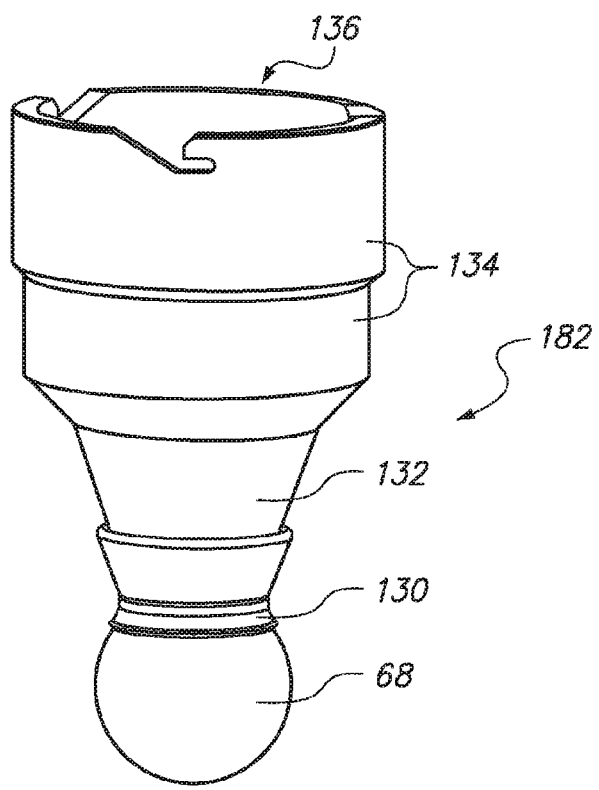
Figure 3C:
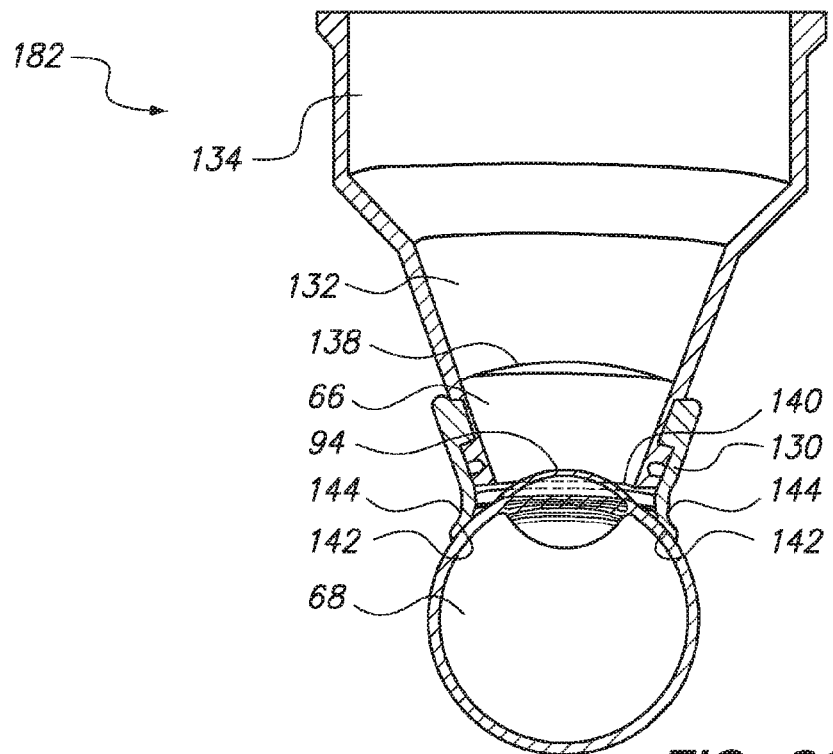

FIG. 3A illustrates a similar configuration, with the patient interface (182) removably coupled to the movable portion (160) of a diagnostic and interventional system. FIG. 3B shows a closer up orthogonal view of a patient interface (182) such as that depicted in FIGS. 2C and 3A. The proximal aspect of the cylindrical upper housing portion (134) forms a geometric coupling interface (136) configured for removable coupling with the movable portion (160) of a diagnostic and interventional system. FIG. 3C illustrates a cross sectional view of the embodiment of FIG. 3B to show the position of the focusing lens (66) within the conical lower housing portion (132) as well as the direct interfacing of the distal surface (140) of the lens (66) with the cornea and/or sclera (94), and the cross sectional features of the flexible (in one embodiment comprising a flexible material such as silicone) eye tissue interface (130), including a cross-sectionally bi-lobed contact surface (142) that creates a vacuum channel (142) between the two lobes which may be utilized to removably couple the interface (130) to the surface of the cornea and/or sclera (94) with an applied vacuum condition such as between about 300 and 600 mm of mercury. In one embodiment, the distal surface (140) of the lens (66) has a radius of curvature equal to about 8.3 mm, which is slightly larger than that of the average human cornea, to provide an engagement configuration wherein the distal surface (140) may be slowly engaged with the cornea at approximately the center of the distal surface (140), and then with increased engagement and very slight applanating loads, bubbles and fluids squeezed outward from the center of contact, ultimately resulting in a relatively clean interfacing for diagnostic and interventional purposes. The shape of the cornea (94) in the depiction of FIG. 3C is the unloaded (un-applanated) shape, to illustrate that there is an intentional mismatch between the distal surface (140) and the unloaded corneal shape in the depicted embodiment (in an actual loaded scenario, the surfaces would directly meet, as described above).

Figure 4A:
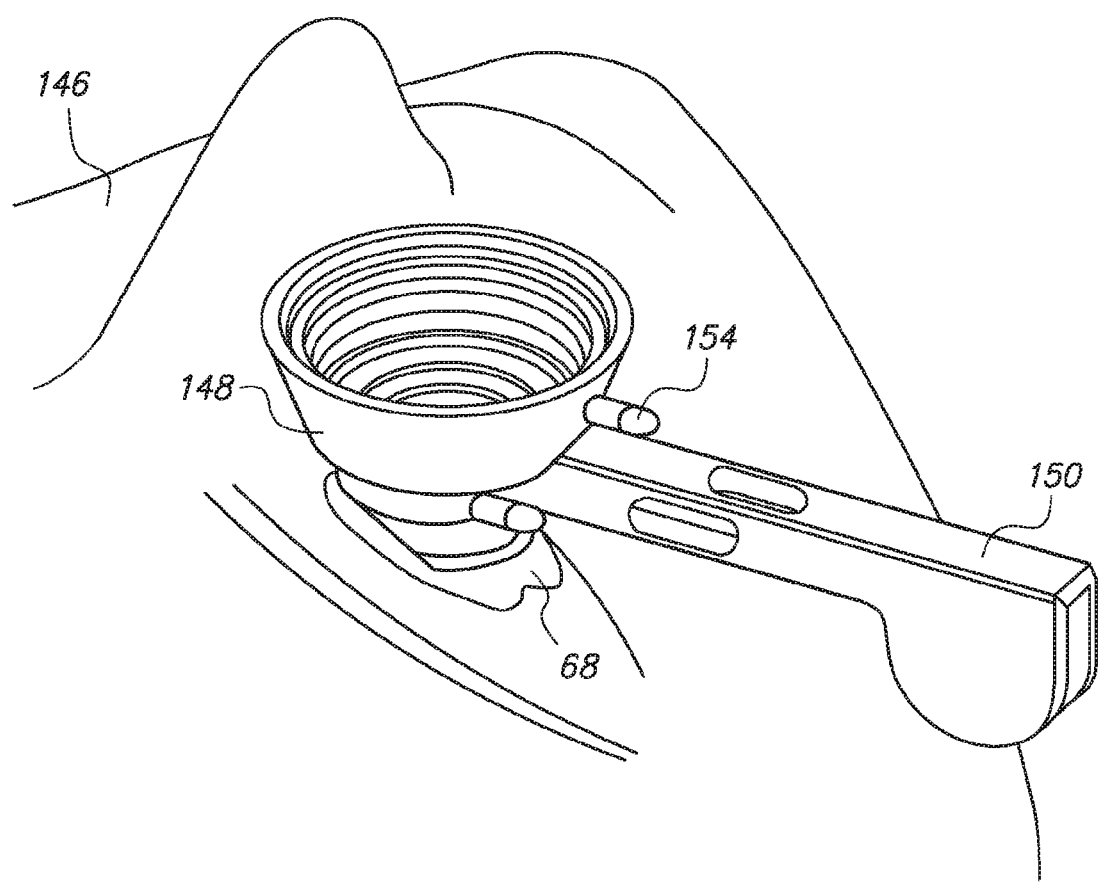
FIGS. 4A-4E illustrate aspects of two-piece patient interface embodiments.
Figure 4B:
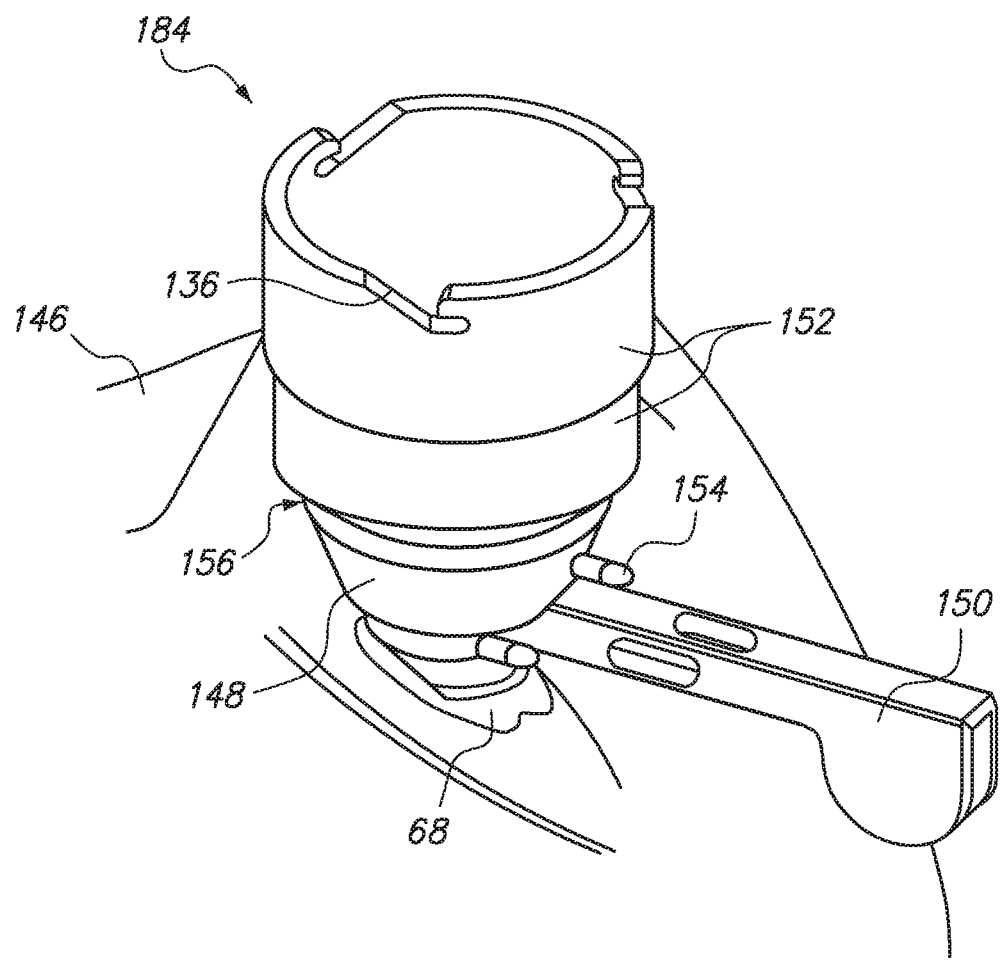
Figure 4C:
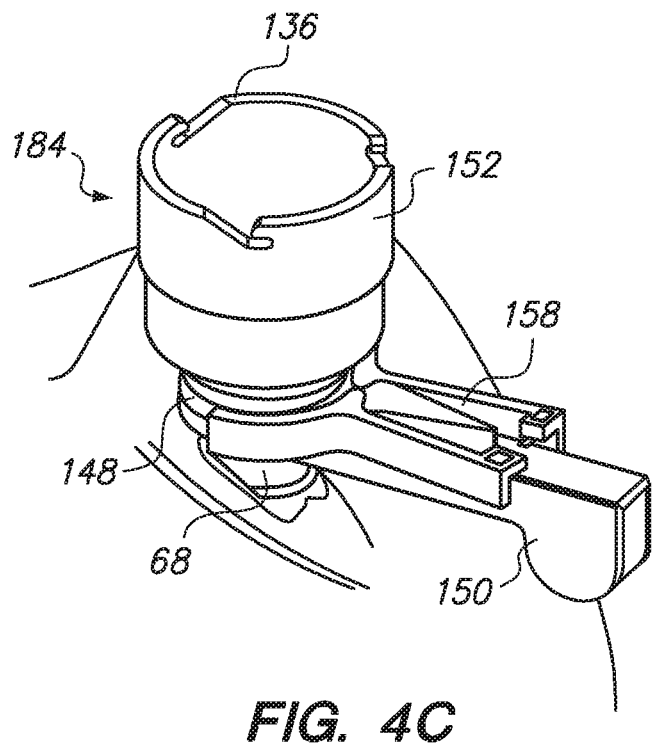
Figure 4D:
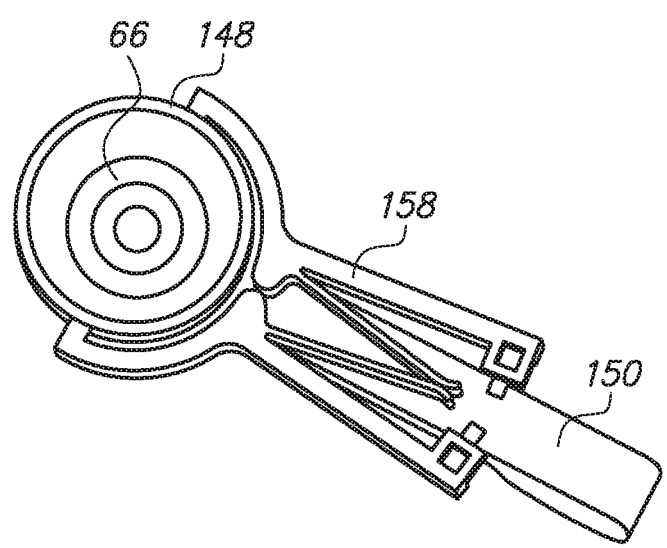
Figure 4E:
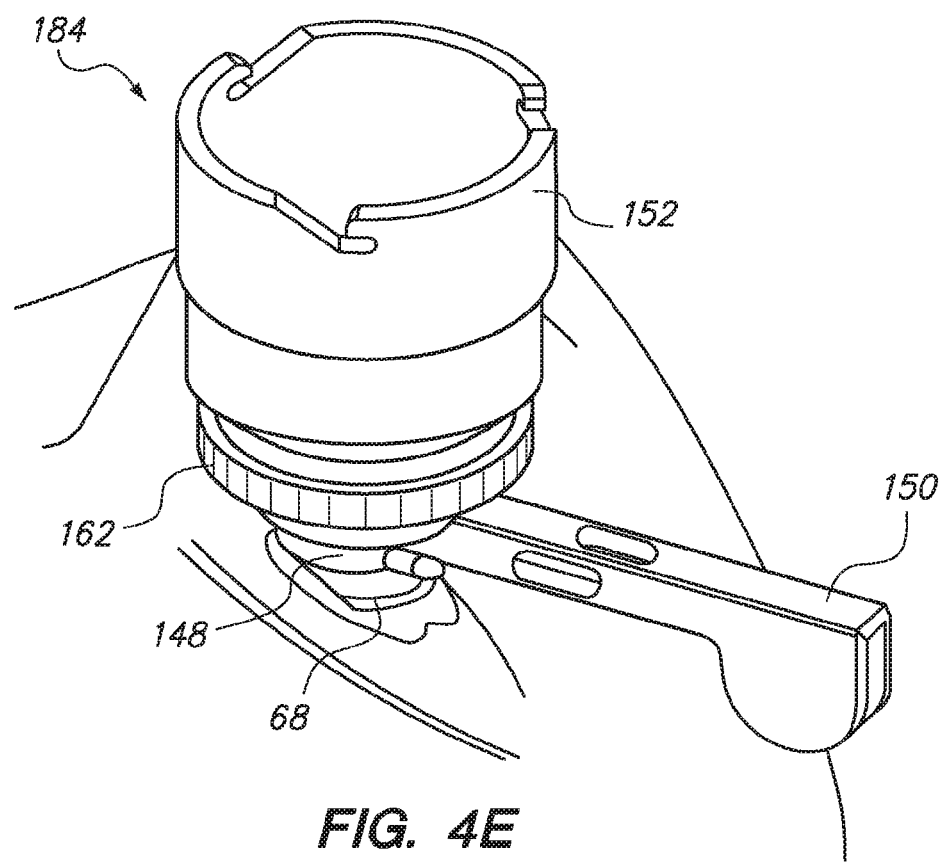

Referring to FIGS. 4A-4E, another embodiment (may be referred to as a "two-piece" embodiment) is depicted, wherein a configuration such as that shown in FIGS. 2C-3C may be deconstructed or decoupled to provide for convenient hand-manipulated placement (i.e., through the use of a lightweight handle 150) of the bottom portion (148) before subsequent coupling with the top portion (152) and movable portion (160) of a diagnostic and interventional system. Together, the top and bottom portions (152, 148) may comprise a "hollow reservoir housing" which defines an interior volume and is configured to be interfaced to the eye as described herein. The top and bottom portions may be removably coupled to each other using a vacuum coupling interface, an interference fit (i.e., press fit) interface, an electromagnetic coupling interface (i.e., wherein a current is applied to enforce a junction, and the current may be turned off to release the junction), a manually-actuated mechanical interface (i.e., wherein a latch or fitting may be manually actuated or moved to enforce a locking or unlocking of the interface), or an electromechanically-actuated mechanical interface (i.e., wherein a latch or fitting may be electromechanically actuated or moved, such as by a solenoid or other actuator, to enforce a locking or unlocking of the interface). Referring to FIG. 4A, a patient's face (146) and eye (68) are shown with a bottom portion (148) coupled to the cornea and/or sclera of eye (68) using vacuum loads applied using a vacuum port (154) to bring a flexible interface such as those shown in FIGS. 2C-3C into releasable engagement with the cornea and/or sclera. The lower portion shown is FIG. 4A has relatively low mass and low moment of inertia, and may be manipulated easily by hand into a desired position, after which vacuum may be applied through the port (154) to create the temporary engagement. Subsequently, the top portion (152) may be coupled to the bottom portion (148) with a mechanical interfacing (156) that may comprise a slight interference fit (i.e., such as a snap fit), to form an assembled two-part patient interface (184) which may be coupled to a movable portion (160) of a diagnostic and interventional system, as described above. FIGS. 4C and 4D depict another interfacing embodiment wherein a spring clamp (158) may be utilized to removably couple the bottom portion (148) and top portion (152). FIG. 4D is a cross sectional view of the embodiment of FIG. 4C. FIG. 4E depicts another interfacing embodiment wherein a rotatable collet type coupling member (162) may be utilized to removably couple the bottom portion (148) and top portion (152), by hand-manipulated rotation of the coupling member (162) relative to the bottom portion (148).

Figure 5A:
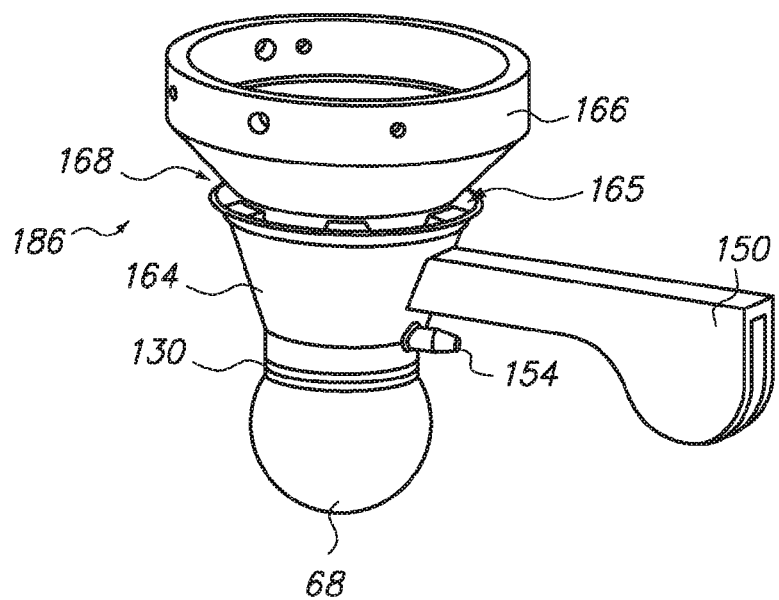
FIGS. 5A-5C illustrate aspects of liquid interface two-piece patient interface embodiments.
Figure 5B:
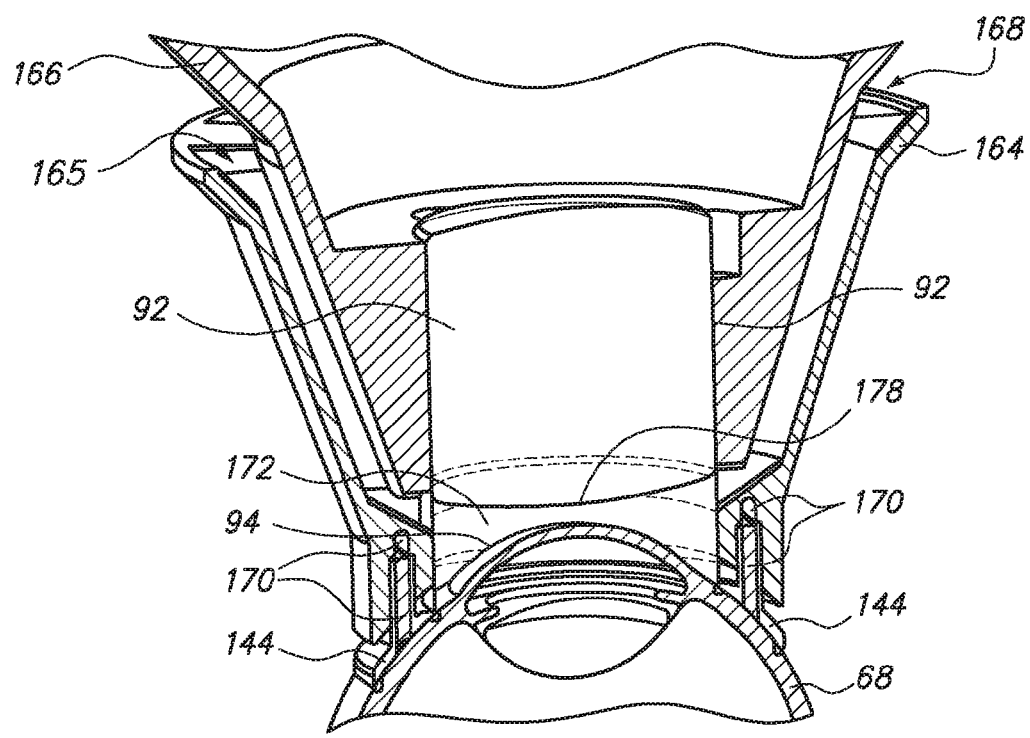
Figure 5C:
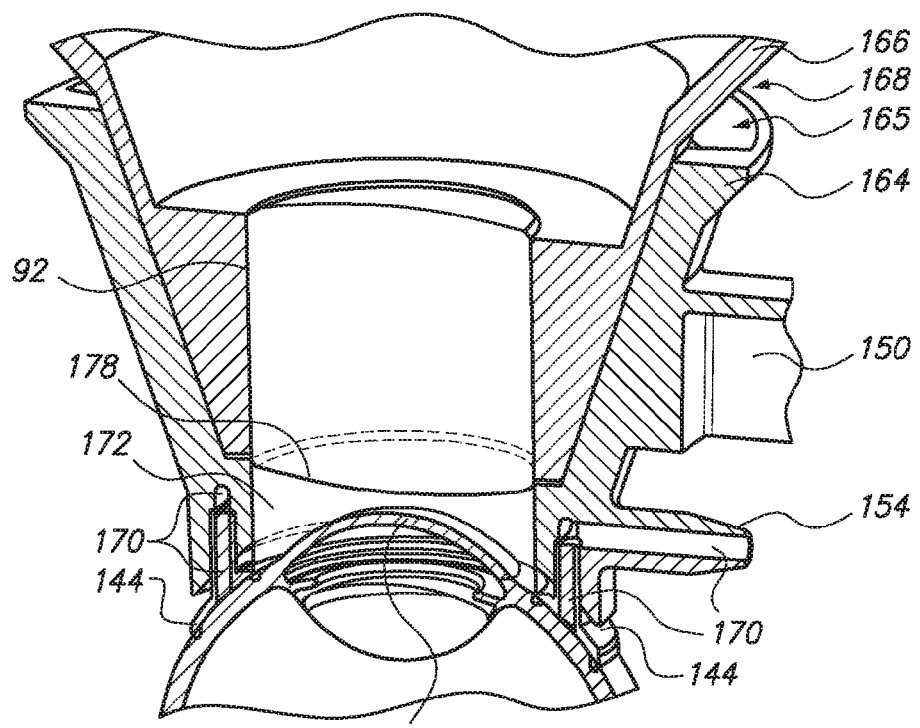

FIGS. 5A-5C depict another two-part patient interface (186) embodiment (this embodiment may be referred to as a liquid interface two-part embodiment), comprising an optical element such as a focusing lens element (92) similar to those described above (element 66) with the exception that the distal surface (178) of the focusing lens element (92) does not come into direct contact with the surface of the cornea (94) and/or sclera—rather, there is a liquid layer (172) interposed between the distal surface (178) of the focusing lens element (92) and the cornea (94) and/or sclera. The optical element (92) may have proximal and distal surfaces, and the distal surface may be a convex surface. In one embodiment, the distal surface of the optical element (92) is directly interfaced (i.e., submerged or directly exposed to) with the liquid layer, leaving the liquid layer as the unifying connection between the eye and the optical element (92). In one embodiment the liquid layer may comprise about 2 cubic centimeters of liquid. The liquid may comprise a material such as water, saline, oil (such as silicon oil), ophthalmic viscoelastic gel, or perfluorocarbon liquid. In the depicted two-part embodiment, the optical element (92) is fixedly coupled to the top, or proximal, portion (152) of the patient interface; in another embodiment, the optical element (92) may be fixedly coupled to the bottom, or distal, portion (148) of the patient interface. As shown in FIG. 5A, a conical bottom portion (160) is coupled to a flexible interface (130) similar to those described above in reference to the one-part and two-part patient interface configurations. As with the aforementioned embodiments, the flexible interface (130) may comprise a compliant circumferential seal member which may comprise two or more circumferential layers with a vacuum space interposed therebetween to facilitate vacuum-enforced coupling of the seal member against the tissue of the eye (using, for example, a vacuum load between about 200 mm mercury and about 600 mm mercury, which may be applied or generated using a vacuum device such as a regulated mechanical vacuum pump). At least one of the circumferential layers may have a cross sectional shape that is tapered (i.e., with the smaller portion of the taper more immediately adjacent the eye tissue), and at least one of the circumferential layers may comprise a shape that is at least partially spherical (i.e., akin to a slice of a spherical shape). A manual manipulation handle is coupled to the bottom portion (160) to allow for easy coupling of the relatively low mass and inertia bottom portion (160) to the cornea and/or sclera (for example, with coupling retention provided by vacuum through the vacuum port 154) before interfacial (168) engagement of the bottom portion to the top portion (166), which is configured to be removably coupled to a movable portion (160) of a diagnostic and interventional system such as that described in reference to FIG. 1 (for example, using a mechanical coupling interface, vacuum, or other removable coupling means). As shown in FIGS. 5A-5C, the interfacial engagement (168) preferably is configured such that the liquid layer (172) is open to the external environment (i.e., to the atmospheric pressure configuration of the patient examination or operating room) such that additional fluid may be added by direct pour or syringe (i.e., through one of the depicted access features 165); similarly, liquid may be poured out of the un-encapsulated environment by changing the orientation of the patient and/or patient interface relative to gravity and pouring the liquid out (i.e., through one of the depicted access features 165). The access features (165) may comprise one or more vents, ports, windows, or the like which provide direct access between the volume defined for the liquid layer (172) and the nearby atmosphere. Such a configuration, which may be deemed an "open configuration" (as opposed to a closed or encapsulated configuration wherein a volume of liquid may be at least temporarily encapsulated within a tank or other structure) wherein the liquid layer (172) has immediate access to the outside environment, is advantageous for several reasons: a) open allows immediate access to the fluid pooled in the patient interface as a liquid layer—which allows for easier filling, refilling, and draining; b) open allows for fluid to escape when coupling a two-part design; without such easy escape, unwanted interfacial pressures may be built up and/or accumulated; c) open allows for gas to more easily escape, and gas typically manifests itself in the liquid layer environment as bubbles, which suboptimally change the optical scenario (i.e., they distort the treatment beam fidelity, and may cause opacities or other unwanted optical distortions). FIGS. 5B and 5C show two slightly different cross sectional views of the embodiment of FIG. 5A. Referring to FIG. 5B, a liquid layer (172) is shown interposed between the distal surface (178) of the focusing lens (92) and the cornea (94) and/or sclera, which are not in physical contact with each other. The liquid layer (172) acts as a light-transmissive medium. In the depicted embodiment, the liquid layer freely floats in the bottom portion 164 before interfacial (168) coupling of the bottom portion (164) and top portion (166) (i.e., the liquid layer 172 rests due to gravity in the bottom of the bottom portion 164 after the bottom portion 164 has been coupled to the cornea 94 and/or sclera using the bi-lobed lip portion 144, which may be fed vacuum through the vacuum channels 170 which are connected to the vacuum port 154 shown in FIG. 5C). In one embodiment, the outer diameter of the bi-lobed flexible seals (144) is about 21 mm, and the inner diameter is about 14.5 mm, leaving about 14 mm of clear aperture available for a broad range of interventional laser cutting, including but not limited to corneal incisions such as limbal relaxation cuts, etc. One additional benefit of the liquid interface is that the optical characteristics of the lens element (92) may be optimized without as much regard to the anatomical fit of the proximal and distal face radii of curvature as with the direct-contact style lens elements (for example, element 66 above). Further, there is greater freedom of materials selection for the focusing lens (92). In one embodiment, the focusing lens (92) comprises an approximately 13 mm thick piece of material commercially available under the tradename "BK-7"® from Schott North America, Inc. of Elmsford, N.Y., the lens (92) having an approximately 245 mm convex proximal surface radius of curvature, and an approximately 68 mm convex proximal surface radius of curvature. Additionally, the displacement of the lens (92) away from the cornea (94) and/or sclera better facilitates anterior corneal and/or scleral surface cutting via laser without lens particle contamination. OCT imaging, as available, for example, in the system described in reference to FIG. 1, may be utilized to confirm the dimensions of the fluid gap between the cornea (94) and/or sclera and the focusing element (92). In one embodiment the liquid or fluid layer (172) comprises saline. In other embodiments, liquids may be specified with customized dispersive, refractive, bubble resisting, and other qualities.

In another embodiment, the two main temporarily or removably coupleable portions of the patient interface structure (148, 152) may be more permanently coupled (i.e., either before the procedure, or during manufacturing of the parts wherein they by be fixedly coupled to each other or formed together as one construct), in the form of a "one-piece" liquid-facilitated patient interface, with features identical to those described above in reference to FIGS. 4A-5C, but without the decouplable interface between such portions (148, 152).

Figure 6A:
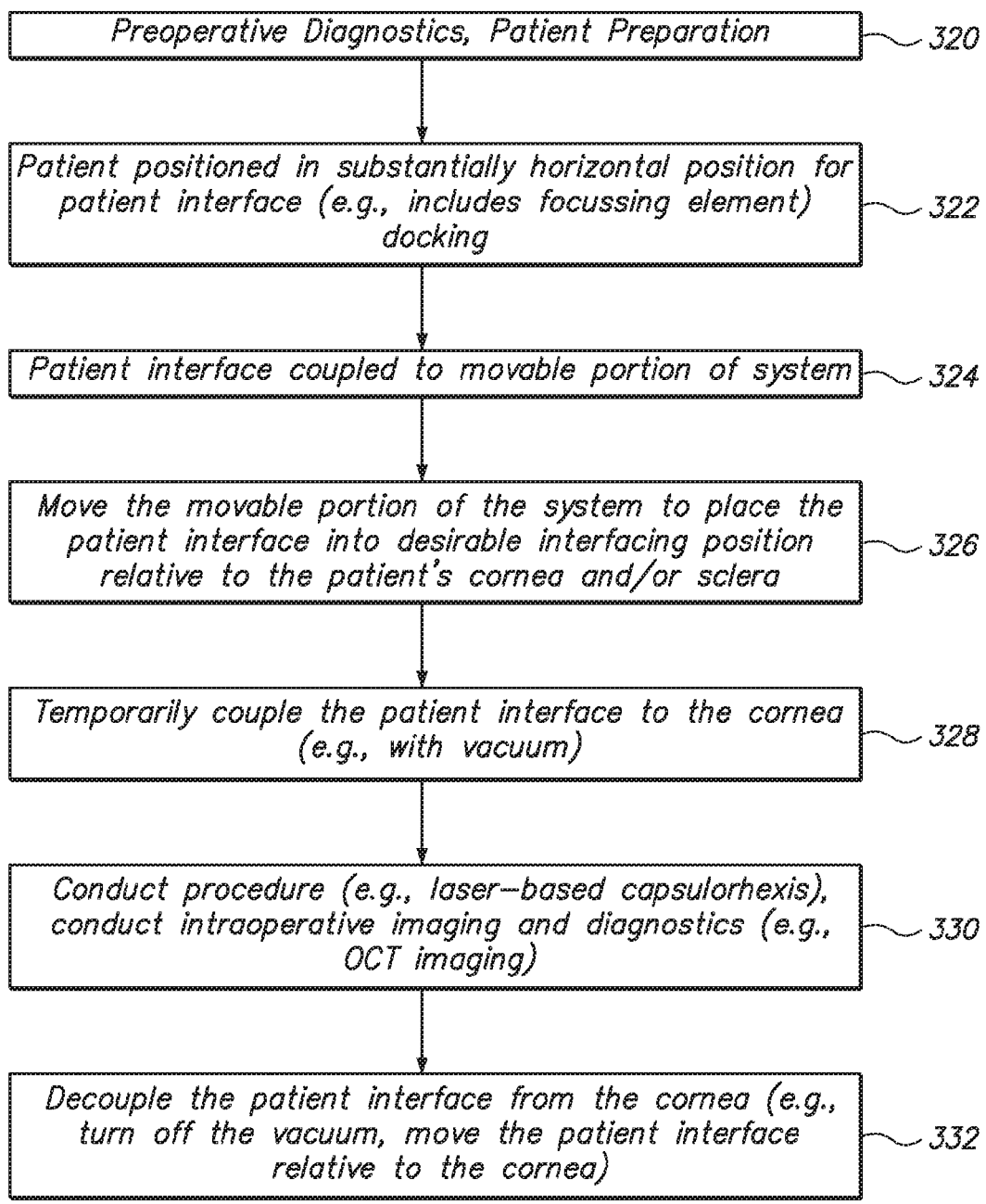
FIGS. 6A-6D illustrate aspects of techniques for utilizing configurations such as those described in reference to FIGS. 1-5C.

Referring to FIGS. 6A-6D, various implementation embodiments utilizing configurations such as those described above are illustrated. Referring to FIG. 6A, subsequent to preoperative diagnostics and patient preparation steps (320), a patient may be positioned in a substantially horizontal position for patient interface docking (322) (i.e., due to the desire to not fight gravity when using a one or two part embodiment; further, in a liquid interface two part embodiment, it is desirable to not have the liquid spill out of the bottom portion). With the patient interface coupled to a movable portion of the system (324) (i.e., by a mechanical interface coupling, vacuum coupling, etc), the movable portion may be utilized to move the patient interface into a desirable interfacing position relative to the patient's cornea and/or sclera (326), where the patient interface may be removably coupled to the cornea and/or sclera (for example, using vacuum, or mechanical load or pressure to create a liquid-tight seal which may also serve to stabilize the eye) (328). With the docking completed, the procedure may be conducted along with intraoperative imaging (330). After completing the procedure, the patient interface may be decoupled (i.e., by releasing the vacuum) from the cornea and/or sclera (332).

Figure 6B:
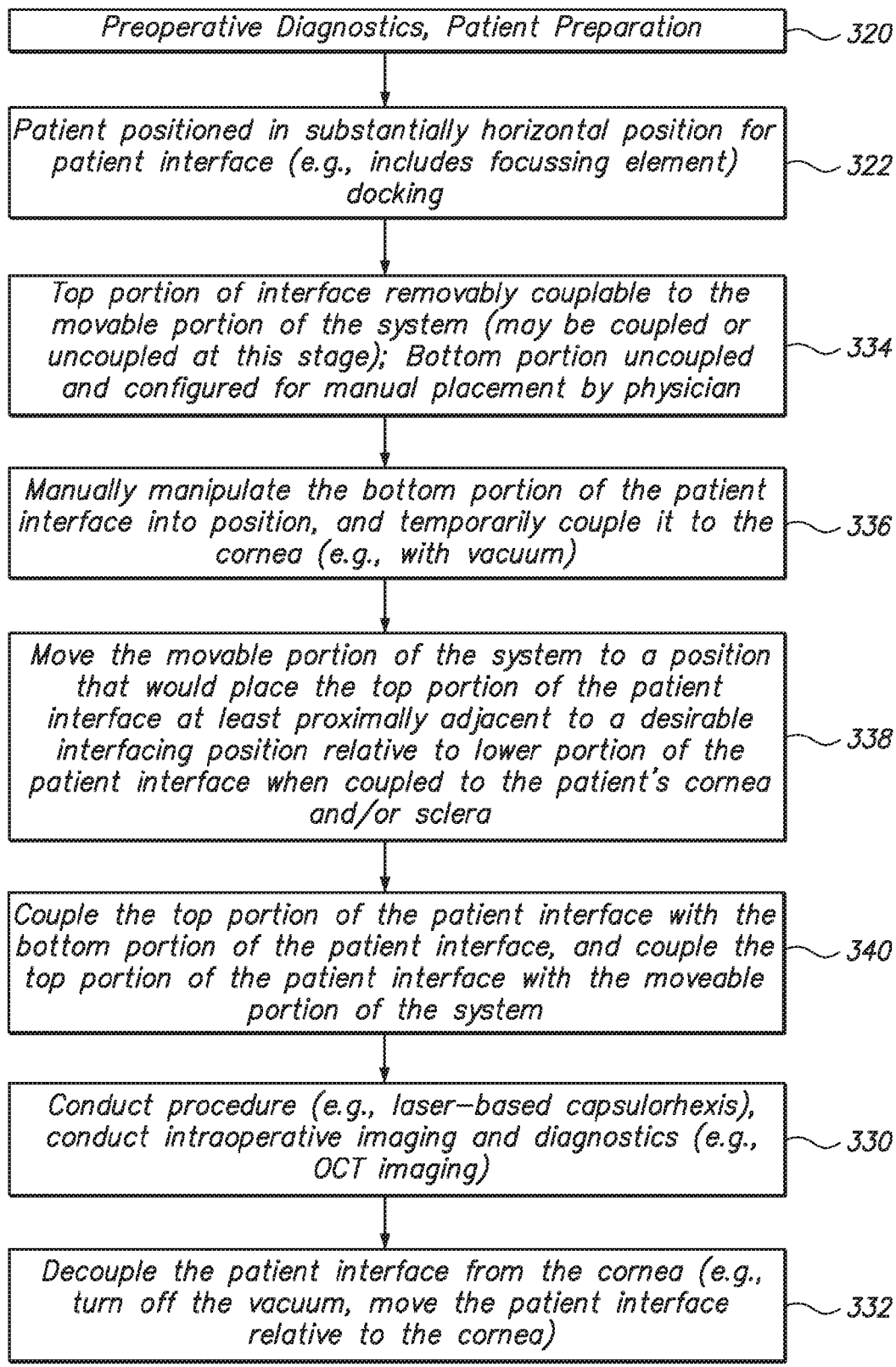

Referring to FIG. 6B, another embodiment is depicted wherein the first two and last two steps are the same as in the embodiment of FIG. 5A, and the intermediate steps comprise providing a two-piece patient interface configuration that is removably couplable to the eye, to itself (i.e., the two pieces), and proximally to the system (334), removably coupling the bottom portion to the cornea and/or sclera (336), moving the system into a position whereby the top portion, when coupled to the bottom portion, may be easily coupled to the system (338), and coupling the top portion to the system (340).

Figure 6C:
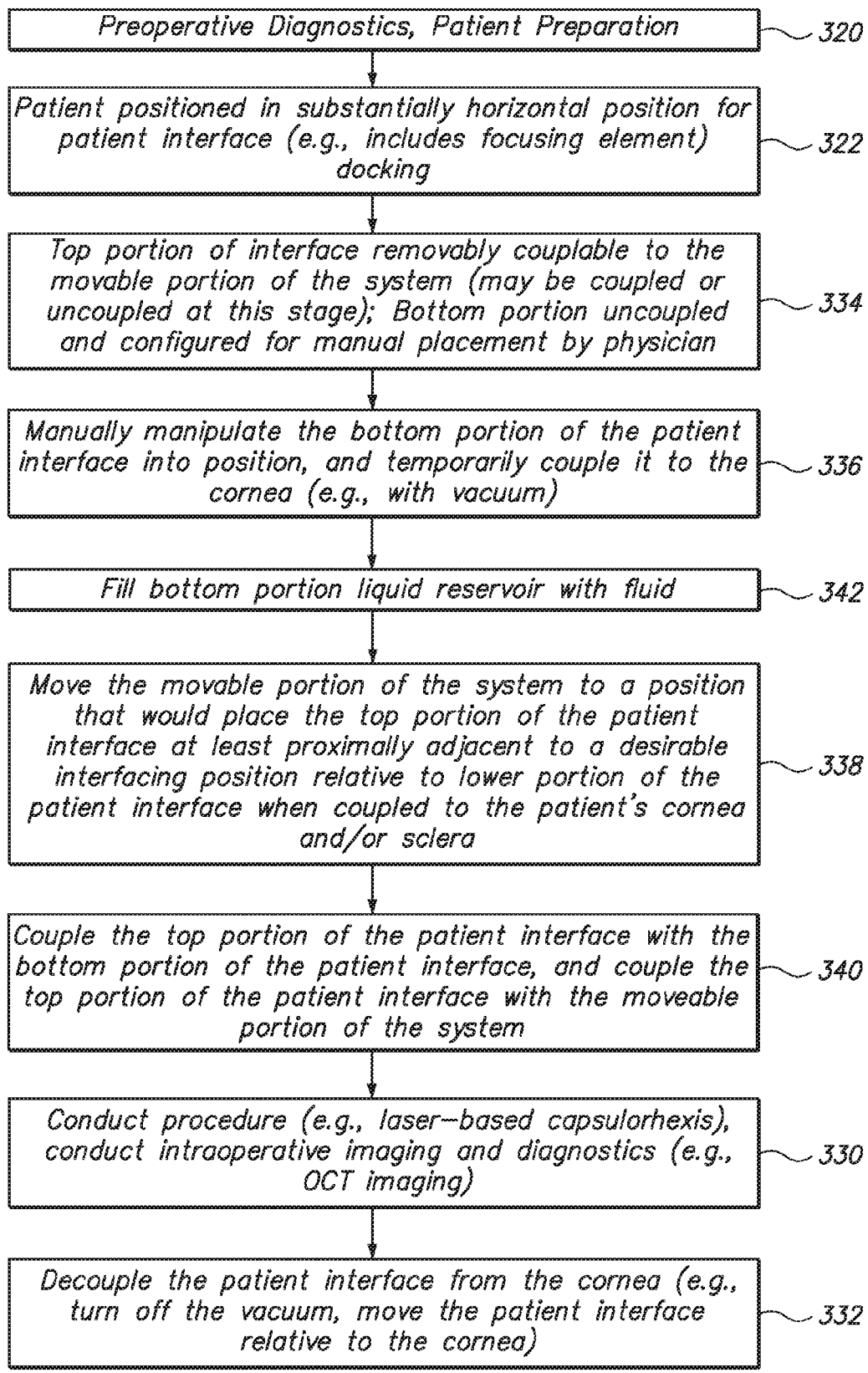
Figure 6D:
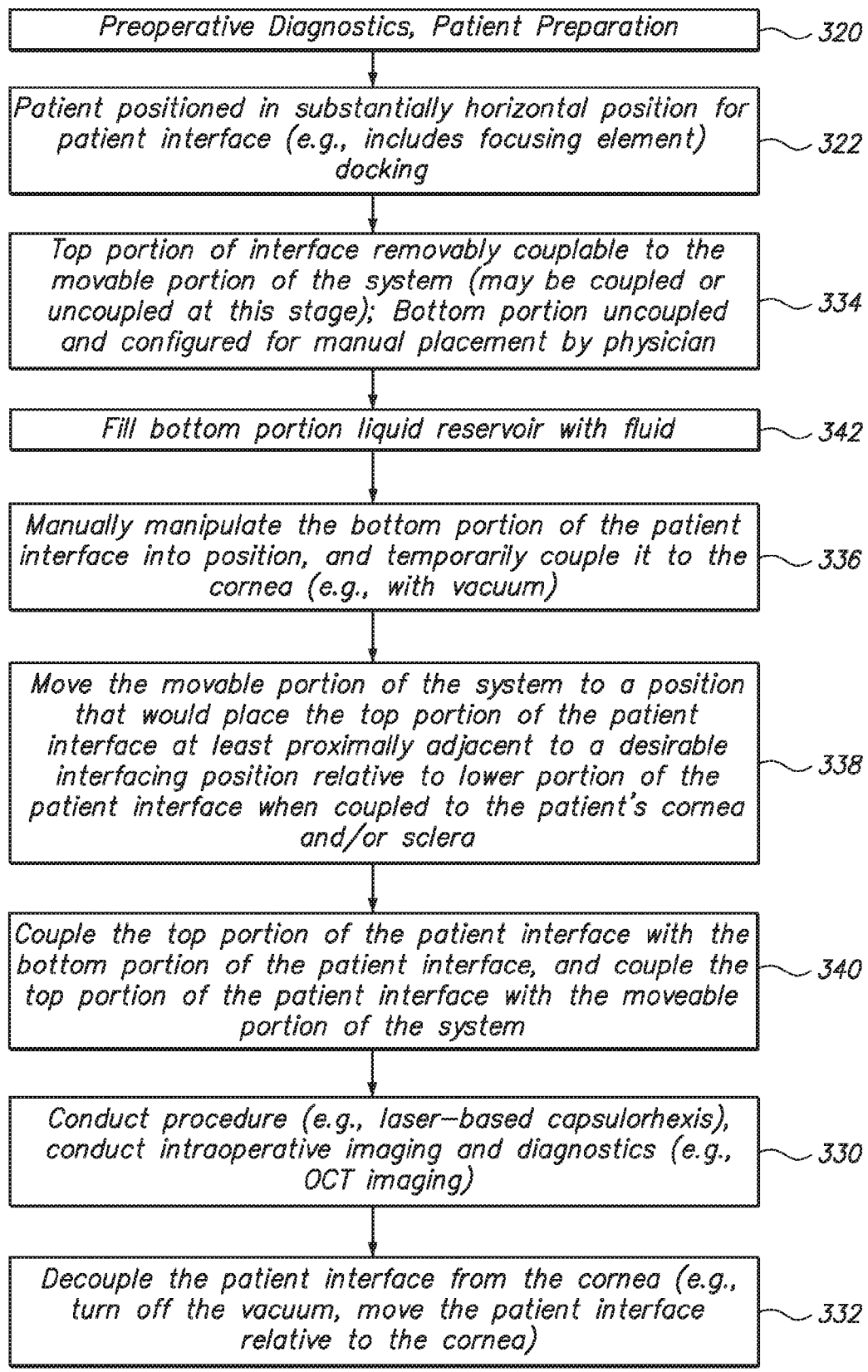

Referring to FIG. 6C, an embodiment is depicted that is similar to that of FIG. 6B, with the addition of an intermediary step 342 (i.e., to accommodate a liquid interface two-part patient interface configuration) of adding liquid (i.e., by pouring it in, injecting it in with a syringe, etc) to the bottom portion after the bottom portion is coupled to the cornea and/or sclera. FIG. 6D illustrates an embodiment similar to that of FIG. 6C, with the exception that the liquid layer may be added (342) before the bottom portion is fully coupled to the cornea and/or sclera (336). Such a configuration may lead to some leakage of fluid between the bottom portion and the cornea and/or sclera and subsequently into the vacuum system.

Figure 7A:
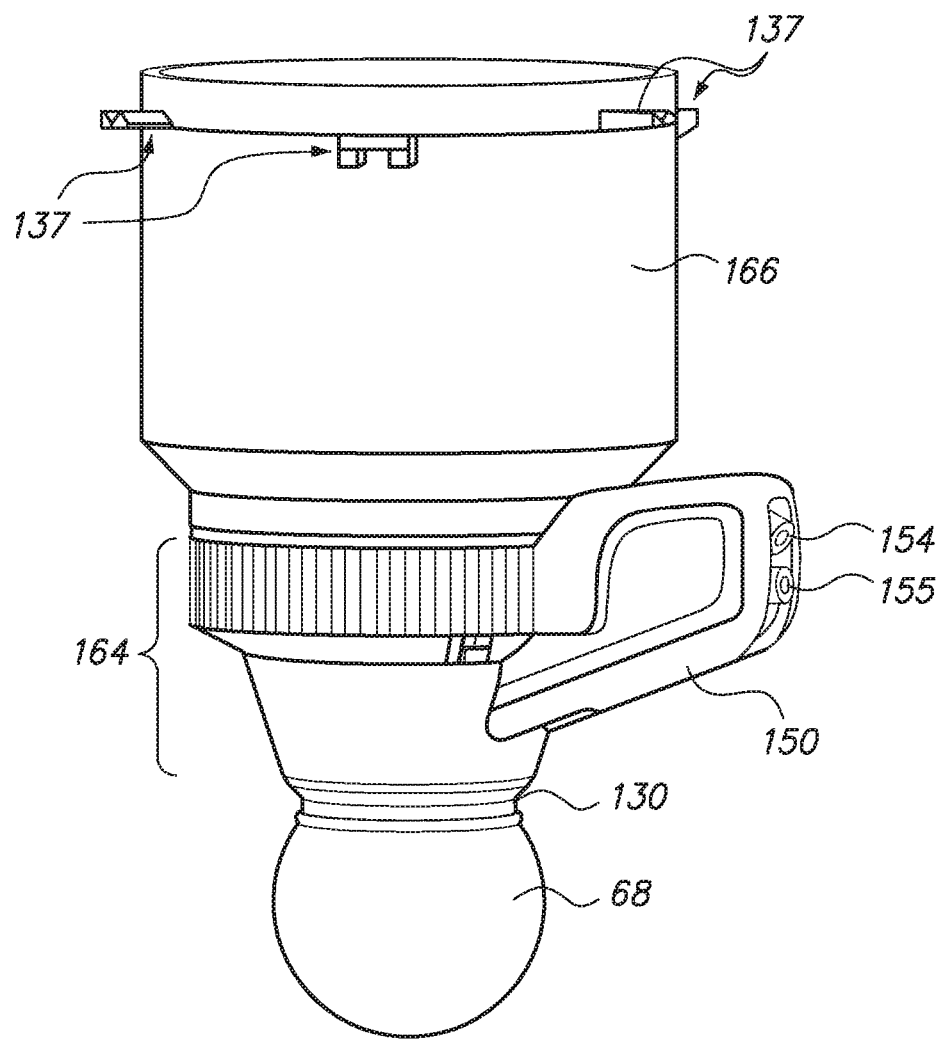
FIGS. 7A-7V illustrate aspects of a patient interface embodiment that features a tissue migration bolster structure interposed between two portions of a sealing structure.
Figure 7B:
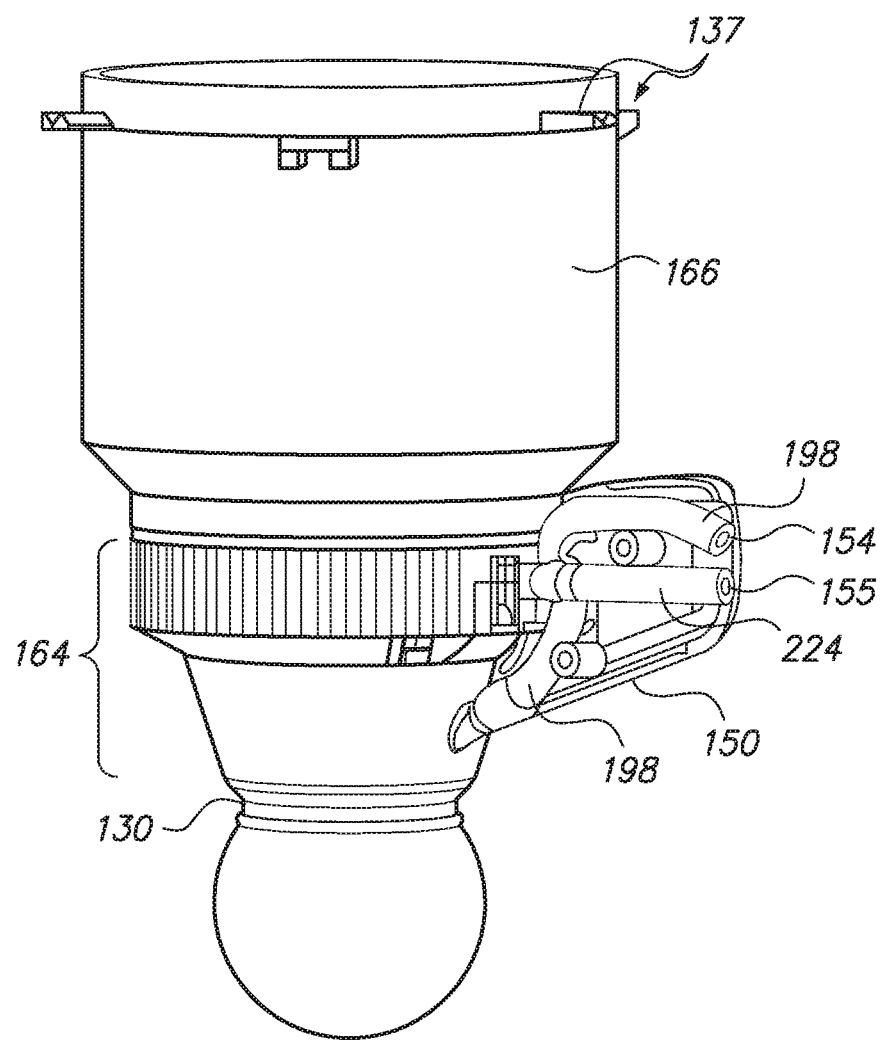
Figure 7C:
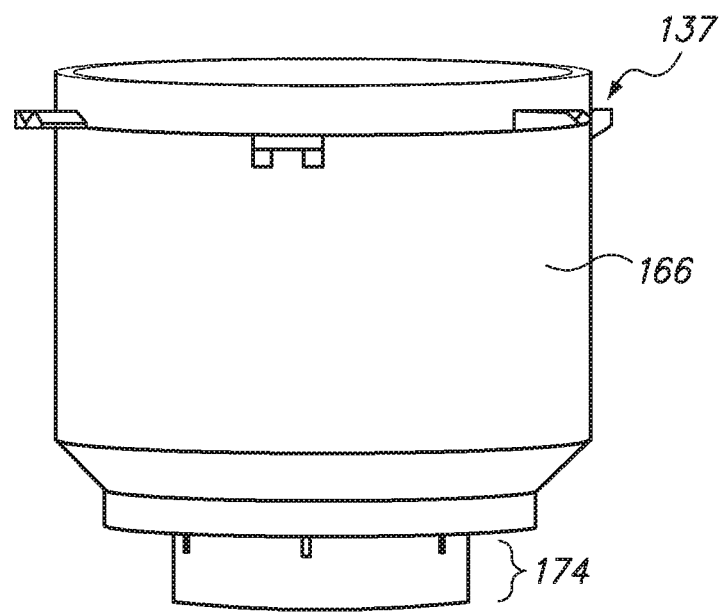
Figure 7D:
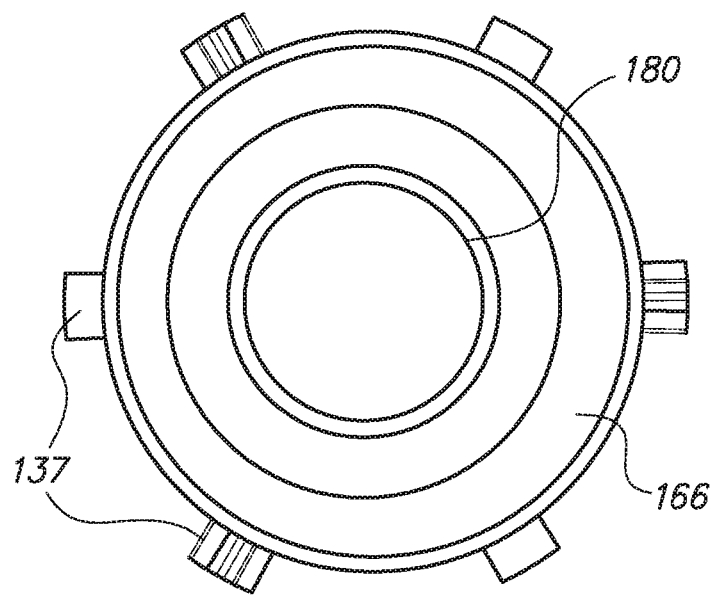
Figure 7E:
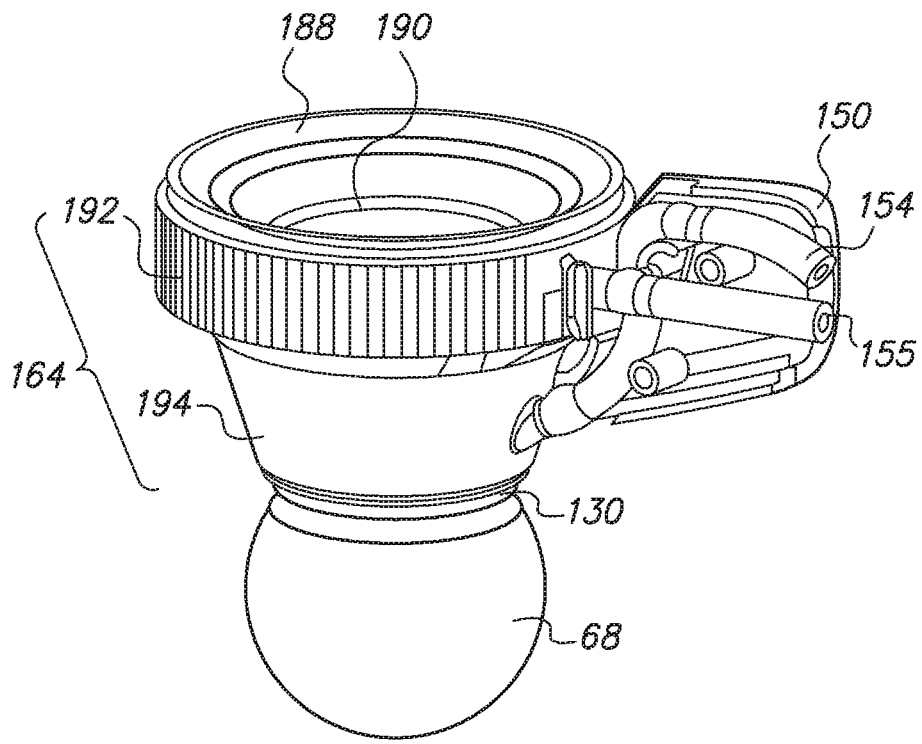
Figure 7F:
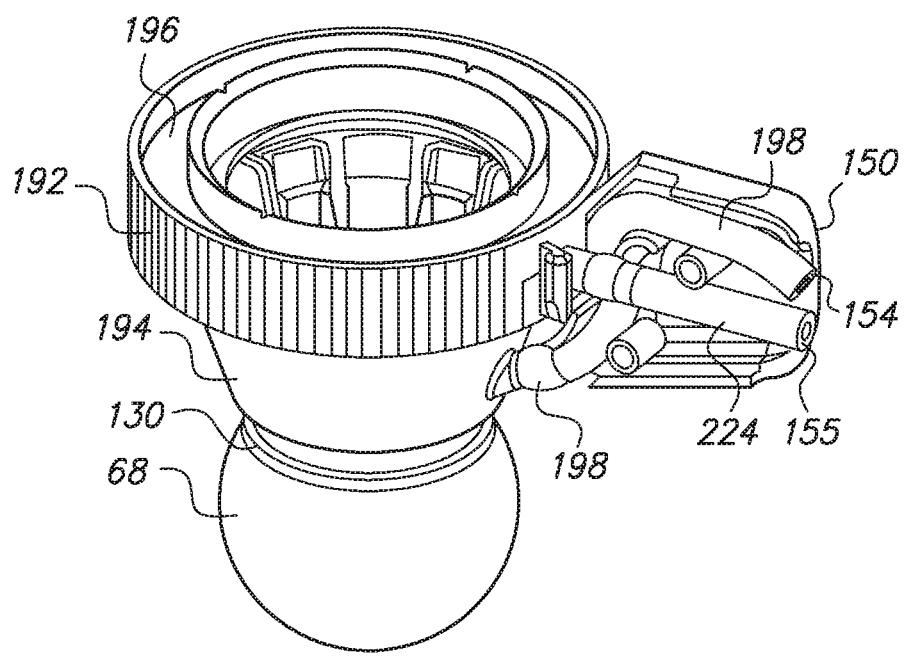
Figure 7G:
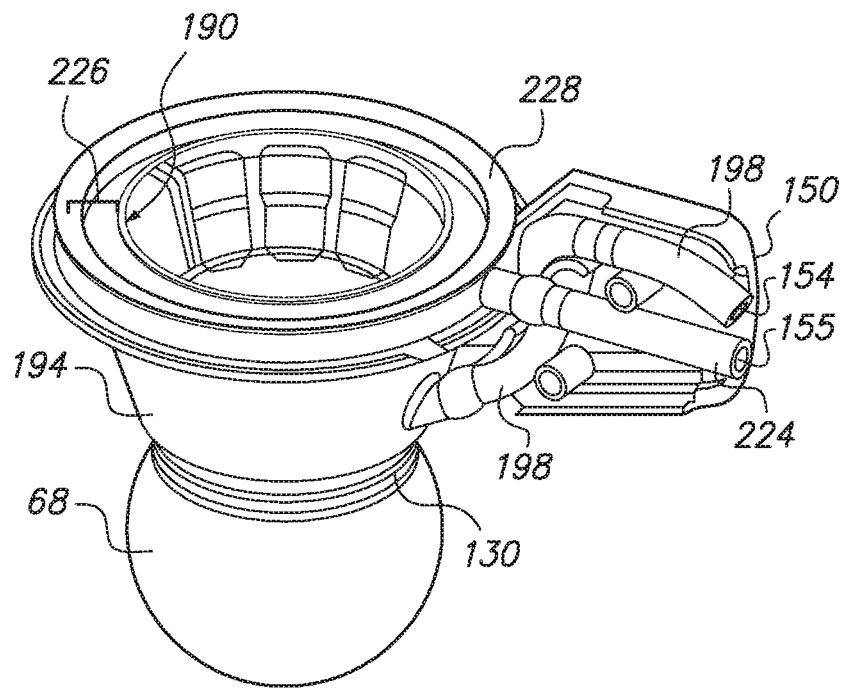
Figure 7H:
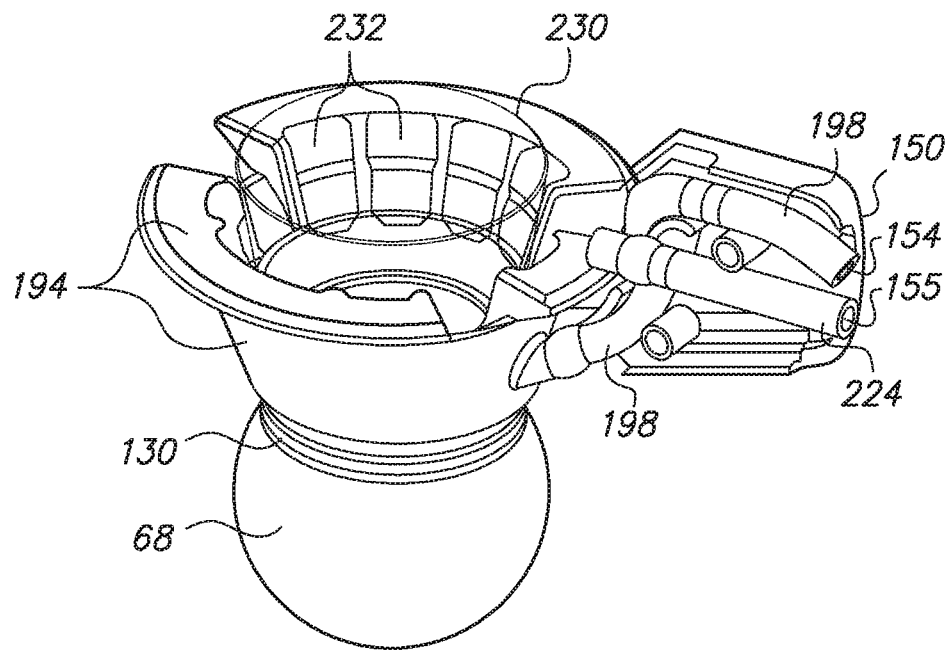
Figure 7I:
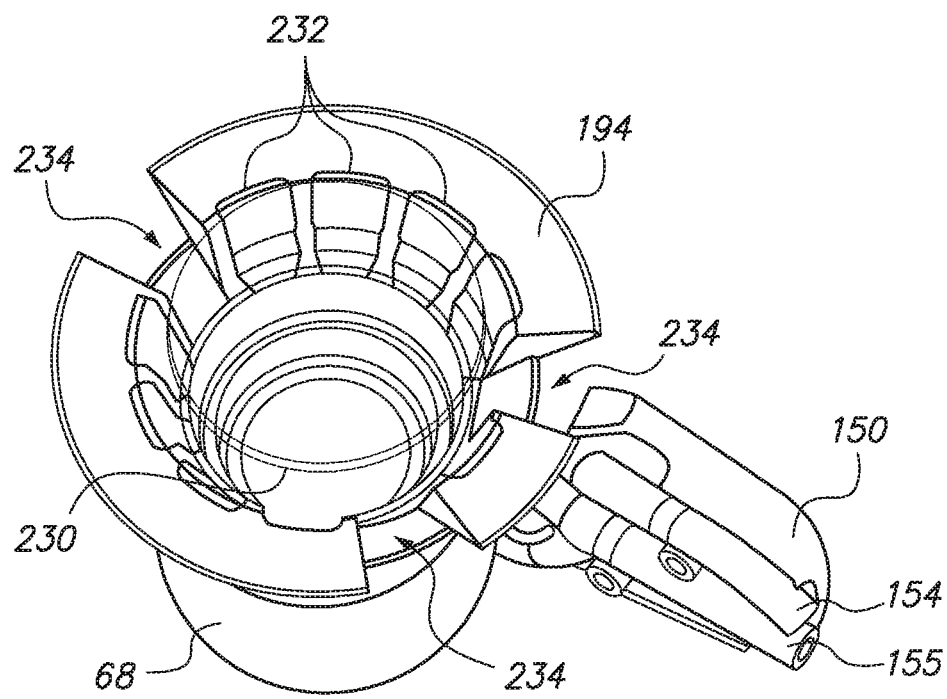
Figure 7J:
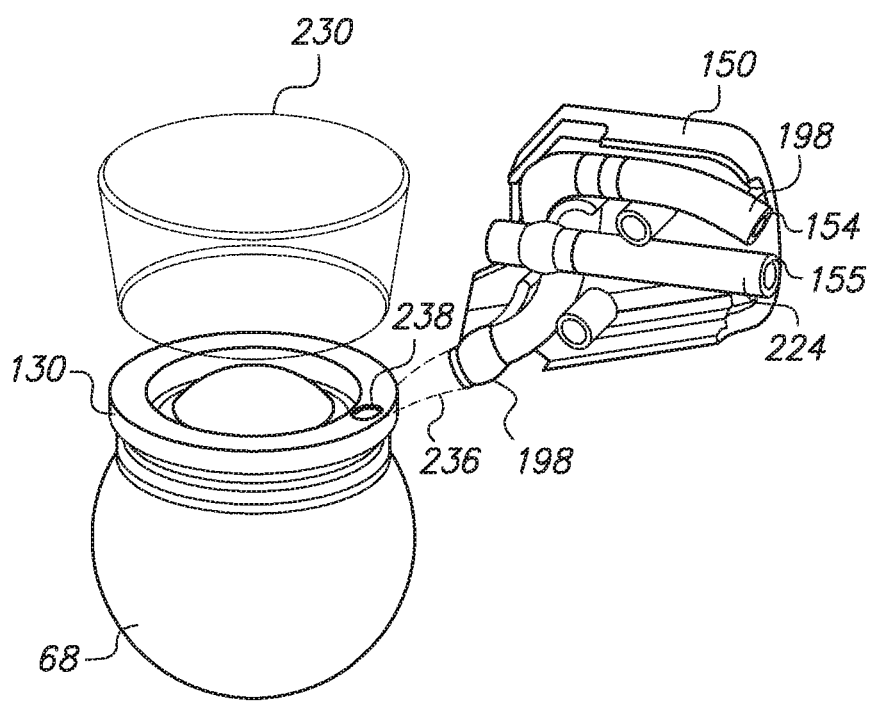
Figure 7K:
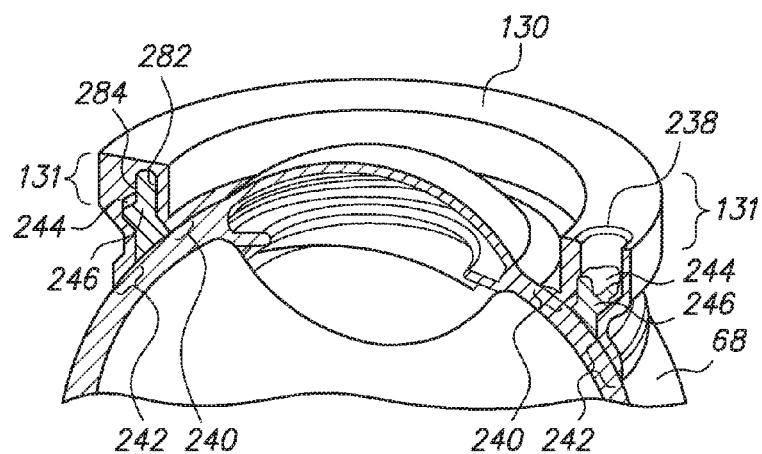
Figure 7L:
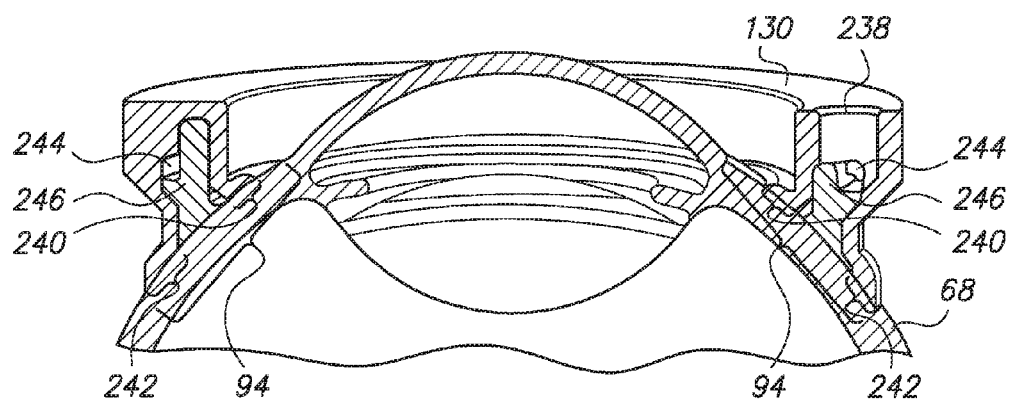
Figure 7M:
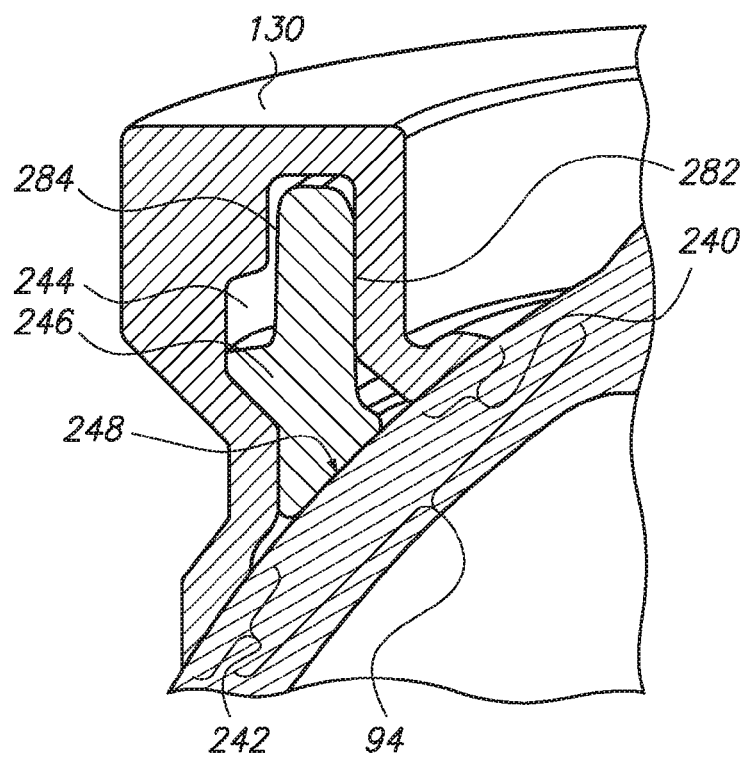
Figure 7N:
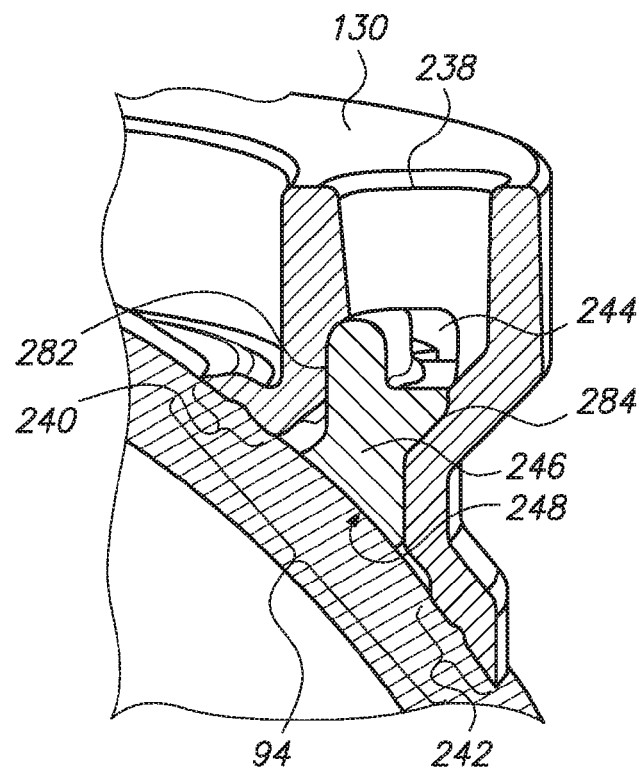
Figure 70:
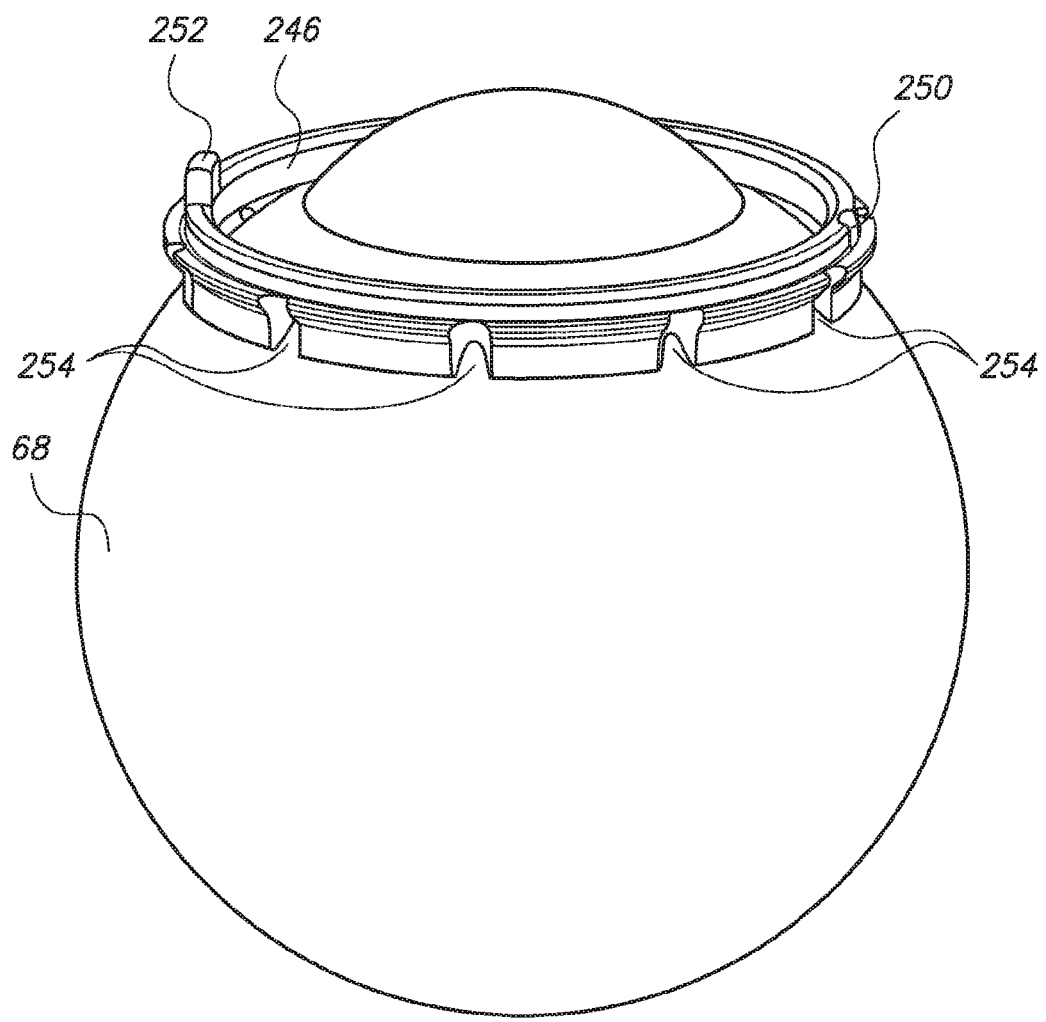
Figure 7P:
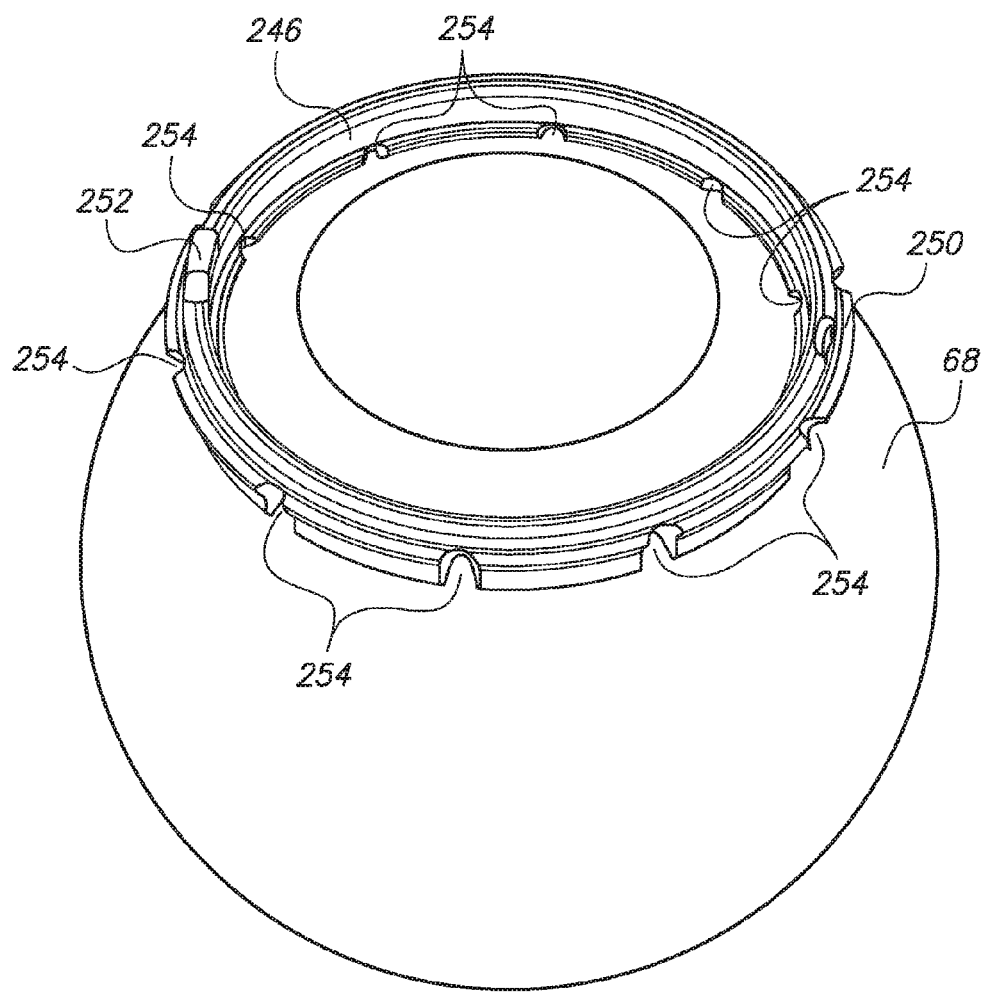
Figure 7Q:
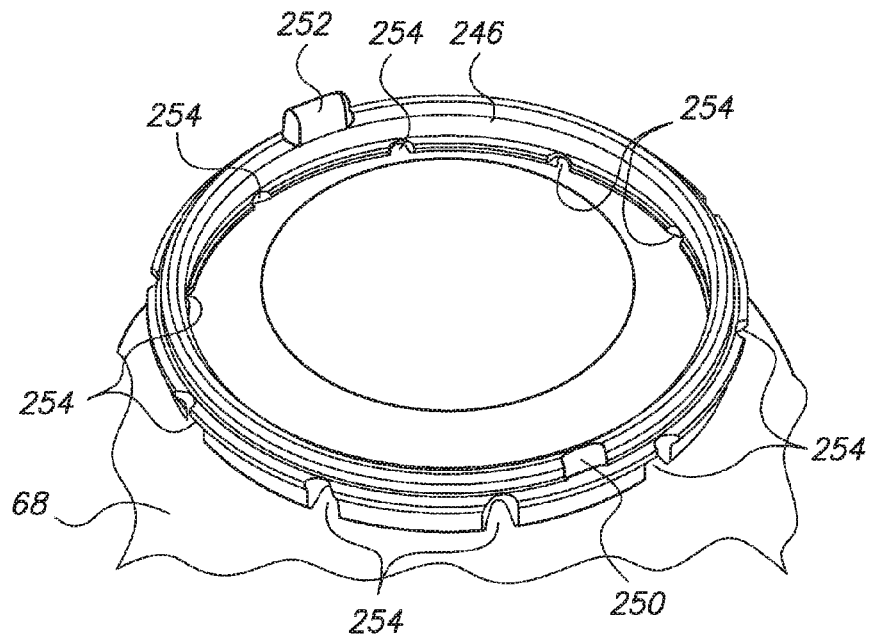
Figure 7R:
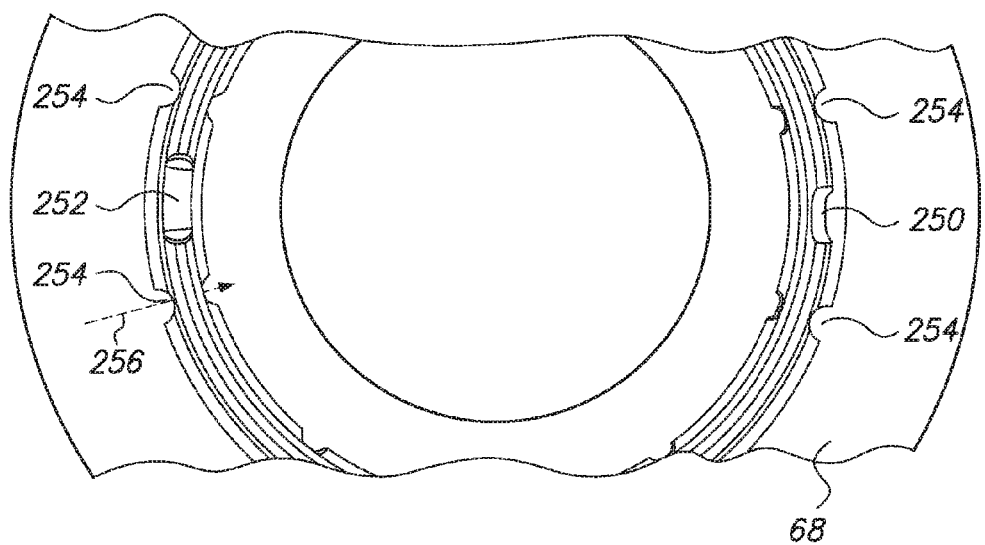
Figure 7S:
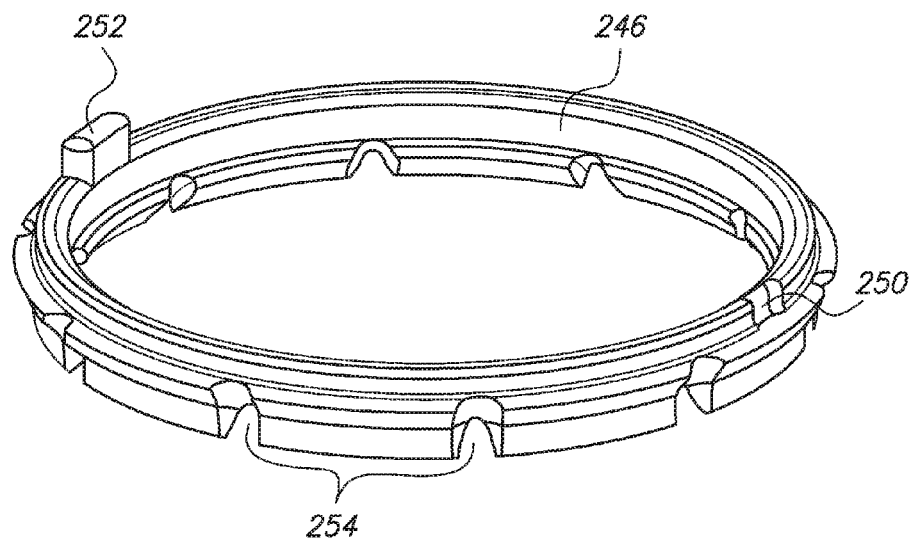
Figure 7T:
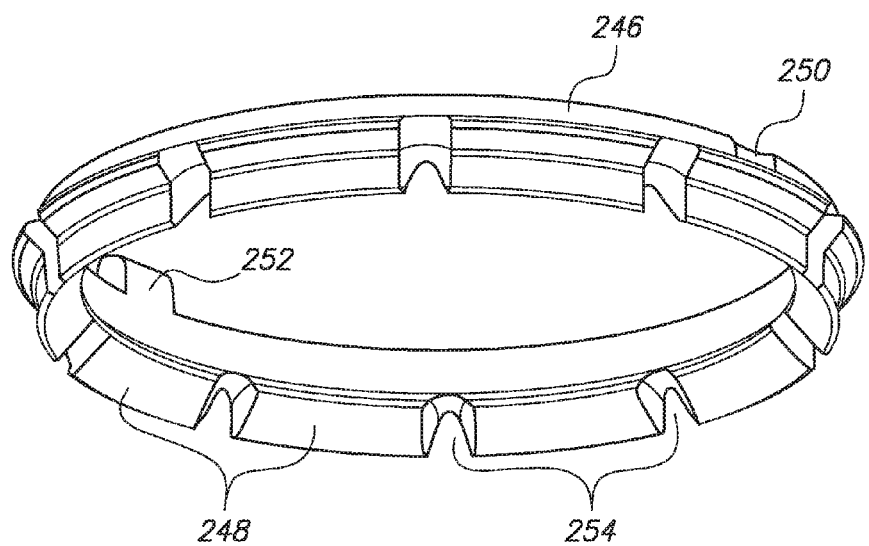
Figure 7U:
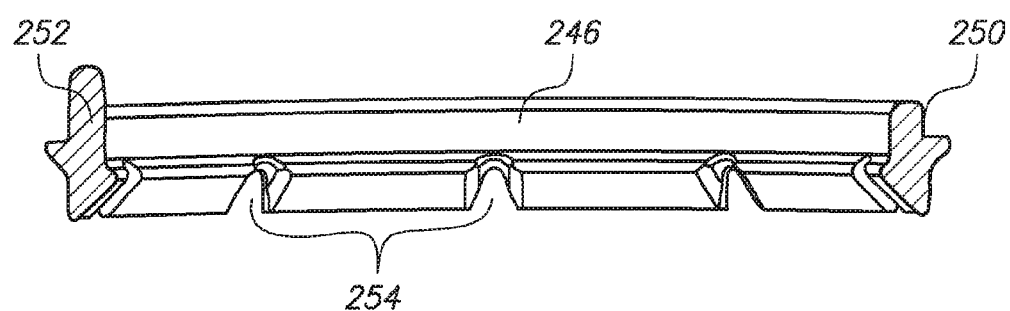
Figure 7V:
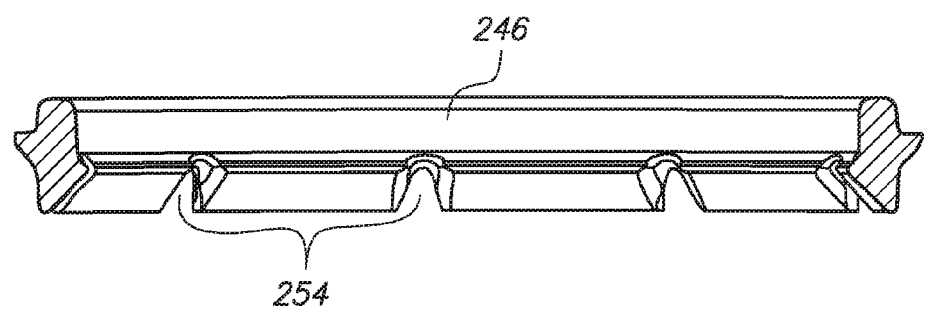

Referring to FIGS. 7A-7V, various aspects of another embodiment of a two-part patient interface configuration are illustrated. Referring to FIG. 7A, a two-part assembly comprising a top portion (166) of a patient interface housing having features (137) configured to be removably coupled to a ophthalmic laser intervention and imaging system, such as that described above in reference to FIG. 1, is depicted removably coupled to a bottom portion (164) of a patient interface housing that is configured to be removably coupleable to both the top portion (166) and the eye (68) of the patient using a interface member (130) configured to be directly engaged to a portion of the cornea and/or sclera of the patient's eye. Also shown is a handle (150) for manipulating the bottom portion (164) directly, as well as two vacuum ports (154, 155) that are passed through the handle (150) housing. Referring to FIG. 7B, with one portion of the handle (150) housing removed, vacuum lines (198, 224) can be seen leading from the vacuum ports (154, 155) to two portions of the patient interface assembly. As described in further detail below, a first line (198) passes a vacuum load from the first port (154) to a vacuum chamber configured to sealably engage the eye (68) to the patient interface, while another line (224) passes a vacuum load from the second port (155) to a coupling engagement interface utilized to maintain coupling of the top portion (166) of the patient interface housing to the bottom portion (164). Referring to FIG. 7C, a distal portion (174) of the top portion (166) of the patient interface housing is depicted to illustrate that a reduced diameter is utilized for the vacuum seal coupling with the proximal aspect of the bottom portion (164) of the patient interface housing. FIG. 7D illustrates a top view through the top portion (166) of the patient interface housing with an aperture (180) defined therethrough, through which interventional (i.e., such as a laser as described above) and imaging (i.e., such as an OCT imaging system, a Scheimpflug system, direct video, direct photo, infrared, ultrasound, confocal microscopy, nonlinear optical imaging, interferometric ranging and imaging, and the like) systems may direct various forms of radiation en route to the eye of the patient. In one embodiment, a so-called "field of view" of an imaging system or imaging device, such as an OCT, Scheimpflug, video, photo, infrared, or ultrasound may be directed at least in part through the aperture (180), and generally also through an aperture formed through the intercoupled bottom portion (164) of the patient interface housing and an associated lens, to access the eye of the patient.

Referring to FIG. 7E, with the top portion (166) of the patient interface housing removed, an upper seating seal (188) is viewable, as is an engagement seal (190) that is configured to engage the distal portion (element 174 of FIG. 7C) of the top portion (166) of the patient interface housing. The bottom portion (164) of the patient interface housing in this embodiment comprises a lower frustoconical portion (194) coupled to an upper cylindrical portion (192). Referring to FIG. 7F, with the upper seating seal (element 188 in FIG. 7E) removed, a seal accommodating feature (196) or trough is shown in the top of the upper cylindrical portion (192). Referring to FIG. 7G, with the upper cylindrical portion (element 192 of FIG. 7F) removed, the engagement seal (190) can be better visualized, as well as the coupling interface for the upper cylindrical portion (element 192 of FIG. 7F) and a vacuum distribution ring (228) configured to transfer a vacuum load from the second vacuum line (224) to the mechanical interface with the bottom portion (164) of the patient interface to cause vacuum-stabilized coupling of the bottom and top portions (164, 166) of the patient interface housing members during use. Referring to FIG. 7H, with the vacuum distribution ring (element 228 of FIG. 7G) and the engagement seal (element 190 of FIG. 7G) removed, the weight-saving relief geometry (232) of the inside of the lower frustoconical portion (194) is shown, essentially comprising a series of relief features cut into the walls of this structure to save weight. An outline is shown to illustrate an access aperture (230) defined through the lower frustoconical portion (194), which continues the access to the eye described above in reference to the aperture (180) through the upper portion (166) of the patient interface housing through which imaging and intervention radiation of various types may be passed. FIG. 7I further illustrates this access to the tissue of the eye (68), and also illustrates three fluid access ports (234) through which water or other fluids, as described above in reference to FIGS. 5A-5C, may be added or removed (i.e., removed by pouring off with re-orientation of the head of the patient relative to gravity down).

FIG. 7J illustrates a further disassembled view depicting the engagement assembly (130) configured to seal the patient interface to the cornea and/or sclera of the eye (68) of the patient using a bi-lobed sealing configuration with a vacuum load. As shown in FIG. 7J, the vacuum load from the first vacuum port (154) may be passed through the first vacuum lead (198), across a lumen defined through a portion of the lower frustoconical portion (element 194 of FIG. 7I) shown here in dashed lines (236), and into a vacuum port (238) on the engagement assembly (130). Referring to FIG. 7K, a cross sectional view is depicted to show that the vacuum load may be passed through the vacuum port (238) and into a vacuum chamber defined as a captured volume between the inner and outer seals, the corneal and/or scleral tissue of the eye (68) of the patient, and the proximal circumferential seal member portion (131) of the engagement assembly (130) that joins the inner seal (240) to the outer seal (242) by virtue of a substantially cylindrical inner seal wall (282) and a substantially cylindrical outer seal wall (284). Also shown in FIG. 7K is a tissue migration bolster structure (246) substantially encapsulated within the vacuum chamber and configured to be positioned circumferentially between the inner and outer seals (240, 242) and to prevent localized migration, or distension, of the tissue of the eye (68) toward the patient interface assembly when a vacuum load is applied and transferred into the vacuum chamber. In other words, the tissue migration bolster structure (246) is configured to form a barrier to block distension of the involved ring of eye tissue when a vacuum load is applied. We have found that with such a structure (246), we are able to apply vacuum loads to enforce coupling of the patient interface assembly to the eye of the patient between about 100 mm and about 500 mm of mercury without unacceptable distension. As described above relative to configurations without this structural element, significantly lower coupling loads are desired to prevent localized distension. Also shown in FIG. 7K is a pressure equalization volume (244) comprising a volume of free space positioned between a tissue migration bolster structure (246) and the proximal circumferential seal member portion (131) of the engagement assembly (130), which is configured to allow for the flow of gases (i.e., such as air or nitrogen) to distribute and equalize the pressure within each of a series of ports (elements 254 in FIG. 7O, for example) as they are fluidly coupled to the vacuum port (238) by such equalization volume (244). FIG. 7L illustrates a similar view as FIG. 7J, with a different orientation to better show the pressure equalization volume (244), and FIGS. 7M and 7N shown further magnified views. In the depicted embodiment, at least a portion of the tissue migration bolster structure (246) substantially fills the width of the vacuum chamber between the inner seal wall (282) and the outer seal wall (284) to form a sealing interface between the equalization volume (244) and the surface of the eye (68). In one embodiment the tissue migration bolster structure (246) is fixedly coupled between the inner seal wall (282) and the outer seal wall (284); in another embodiment it is press fit in between the inner seal wall (282) and the outer seal wall (284); in another embodiment, it is loosely fit in between the inner seal wall (282) and the outer seal wall (284), in which case there is not a sealing interface between the equalization volume (244) and the surface of the eye (68). Preferably the portion of the tissue migration bolster structure (246) that becomes directly engaged with the tissue of the eye (68) forms a spherical surface (248), an in the aggregate, the surfaces of the patient interface assembly directly engaging the tissue of the eye (68) preferably form a spherical aggregate surface that has substantially the same profile as the surface of the eye anatomy, which is generally substantially spherical.

Referring to FIGS. 7O-7V, various aspects of an embodiment of a tissue migration bolster structure are shown in detail without other device hardware engaged. Referring to FIG. 7O, a tissue migration bolster structure (246) is shown engaged with the tissue of an eye (68). A port relief feature (250) is formed to accommodate flow of gases (i.e., air, nitrogen, or the like) in through the port (element 238 of FIG. 7N, for example) to the equalization volume (element 244 of FIG. 7N). Further, orientation confirmation feature (252) is shown which is configured to assist a device assembler to place the tissue migration bolster structure (246) in the correct orientation relative to the port (element 238 of FIG. 7N, for example). A plurality of vents or ports (254) is shown connecting the region of the equalization volume (element 244 of FIG. 7N) to the surface of the eye (68). These small ports, having diameters between about mm and about 2 mm, expose the eye (68) to the vacuum load on a distributed basis, with the substantially spherical engagement surface there to prevent distension that could result without the bolster structure. FIG. 7P illustrates a view similar to that of FIG. 7O, but at a different orientation. FIG. 7Q shows a close-up view similar to that of FIG. 7P. FIG. 7R shows a close-up view depicting with a dashed arrow (256) the path of vacuum access from the region of the equalization volume (element 244 of FIG. 7N), through the depicted port (254) to the surface of the eye (68). FIGS. 7S and 7T show orthogonal views of the depicted embodiment of the tissue migration bolster structure (246), and FIGS. 7U and 7V show cross sectional views of the depicted embodiment of the tissue migration bolster structure (246). Suitable tissue migration bolster structures (246) may comprise metallic materials, such as aluminum, stainless steel, titanium, and alloys thereof or polymers selected from the group consisting of: polycarbonate, polyethylene, nylon, polypropylene, isoprene, and copolymers thereof.

Figure 8:
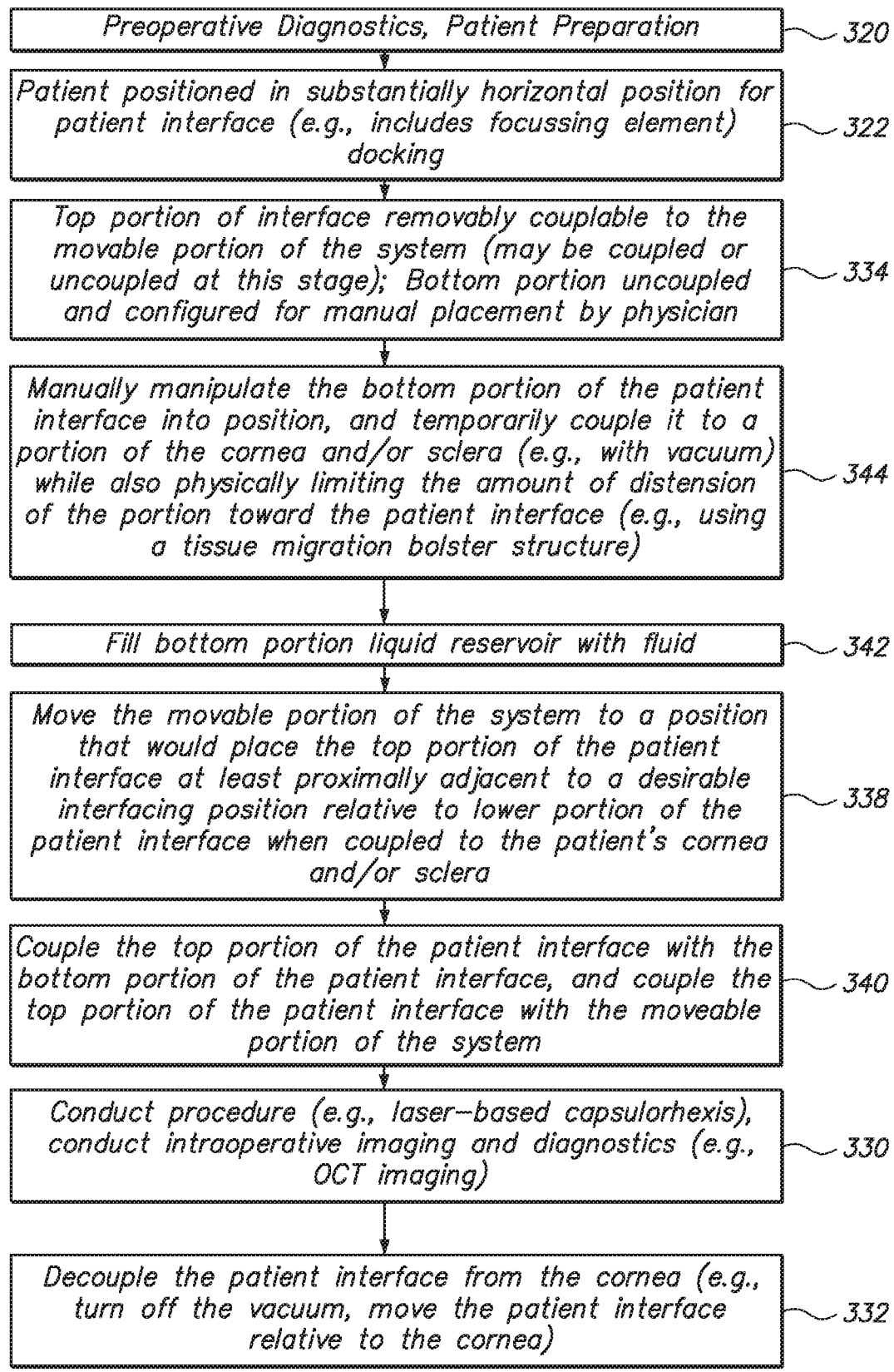
FIG. 8 illustrates aspects of a technique for utilizing configurations such as those described in reference to FIGS. 7A-7V.

Referring to FIG. 8, a technique for utilizing a system such as that described herein in reference to FIGS. 7A-7V is illustrated. As shown in FIG. 8, subsequent to preoperative diagnostics and patient preparation steps (320), a patient may be positioned in a substantially horizontal position for patient interface docking (322) (i.e., due to the desire to not fight gravity when using a one or two part embodiment; further, in a liquid interface two part embodiment, it is desirable to not have the liquid spill out of the bottom portion). The top portion of the patient interface may be coupled to a movable portion of the system (334) (i.e., by a mechanical interface coupling, vacuum coupling, etc). The lower portion of the patient interface may be removably coupled to the cornea and/or sclera, and this coupling may be enforced with a vacuum load, while a mechanical feature of the lower portion of the patient interface physically limits the amount of distension of the immediately associated portion of the eye toward the patient interface (344). With the docking completed, in a two part liquid configuration, fluid may be added to the bottom portion of the patient interface housing to place the surface of the eye within fluid connection to the lens element coupled to the inside of the bottom portion of the patient interface housing (342). The movable portion of the system may be utilized to move (338) the top portion of the patient interface into a position wherein the top and bottom portions of the patient interface may be intercoupled (the junction being enforced, for example, with another vacuum load) (340). The procedure may be conducted along with intraoperative imaging using systems such as confocal microscopy, nonlinear optical imaging, interferometric ranging and imaging, OCT, infrared, light photography, light video, infrared photography or video, ultrasound, Scheimpflug, and the like (330). After completing the procedure, the patient interface may be decoupled (i.e., by releasing the vacuum) from the cornea and/or sclera (332).

Figure 9:
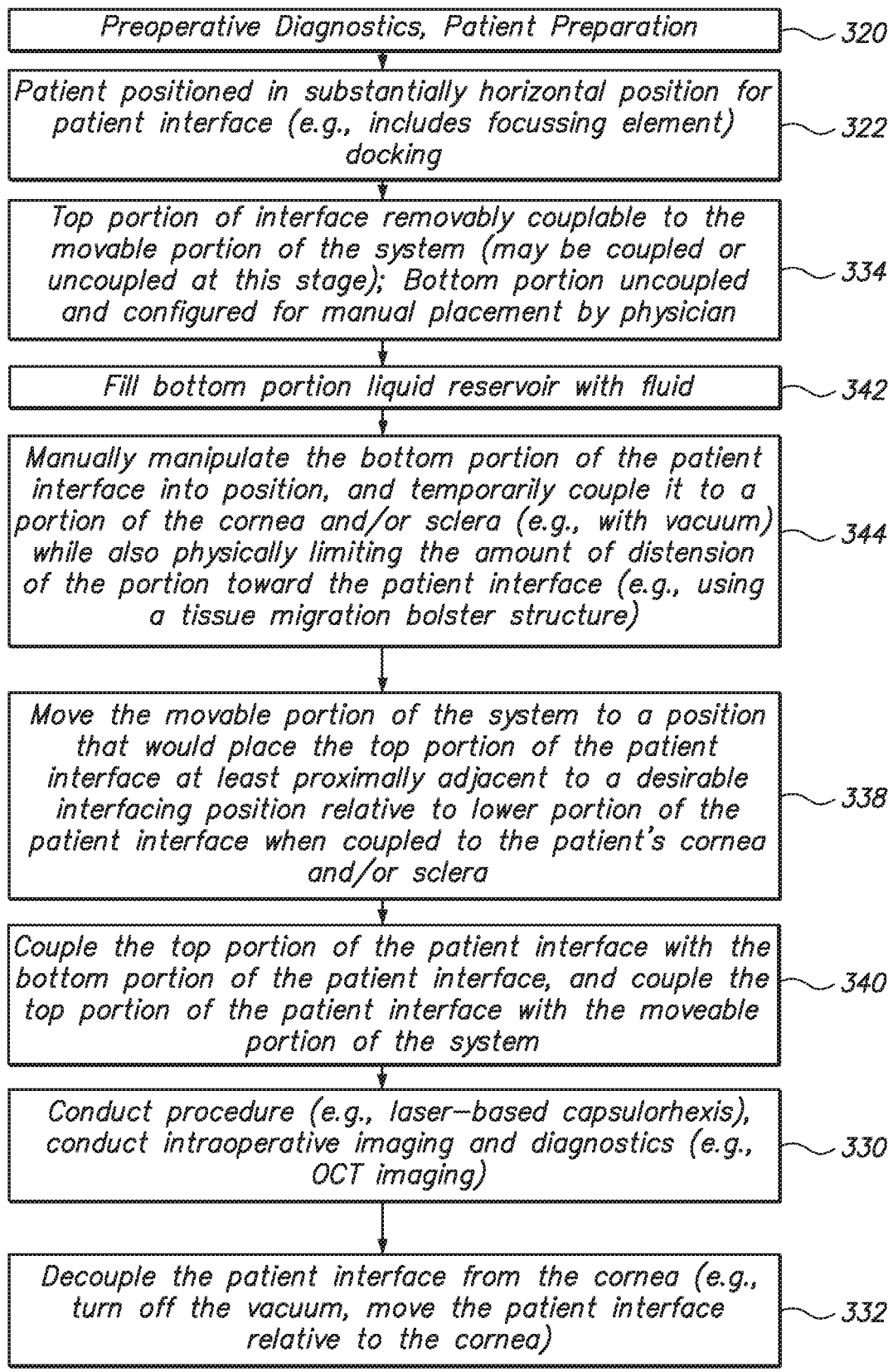
FIG. 9 illustrates aspects of a technique for utilizing configurations such as those described in reference to FIGS. 7A-7V.

FIG. 9 illustrates an embodiment similar to that of FIG. 8, with the exception that the liquid layer may be added (342) before the bottom portion is fully coupled to the cornea and/or sclera (344). Such a configuration may lead to some leakage of fluid between the bottom portion and the cornea and/or sclera and subsequently into the vacuum system.

Referring to FIGS. 10A-10L, various embodiments are shown that may be utilized to assist with the intraoperative determination of eye orientation relative to the instrumentation based upon temporarily marks initially created by a healthcare provider during preparation for an intervention. Conventionally, the provider will conduct a preoperative examination with the patient in an upright position, and will make a series of marks with a pen upon the cornea and/or sclera to provide a temporary reference with regard to the astigmatic axis of the subject eye; this axis may be subsequently utilized during surgery to place relaxing cuts, radial cuts, or other types of incisions, to tailor the geometry of capsular cuts, etc. One of the challenges is that when the patient goes from the upright preoperative environment to being flat on the surface of an operating table during the invention, some re-orientation of the eye is common relative to the position/orientation of the cranium, for example, and the surgeon must find a way to re-establish his understanding of the orientation of the eye anatomy relative to the interventional tools. In one embodiment, a series of fidicual features and/or markers placed within the field of view of the imaging system utilized to view the eye anatomy may be used to establish the eye orientation.

Figure 10A:
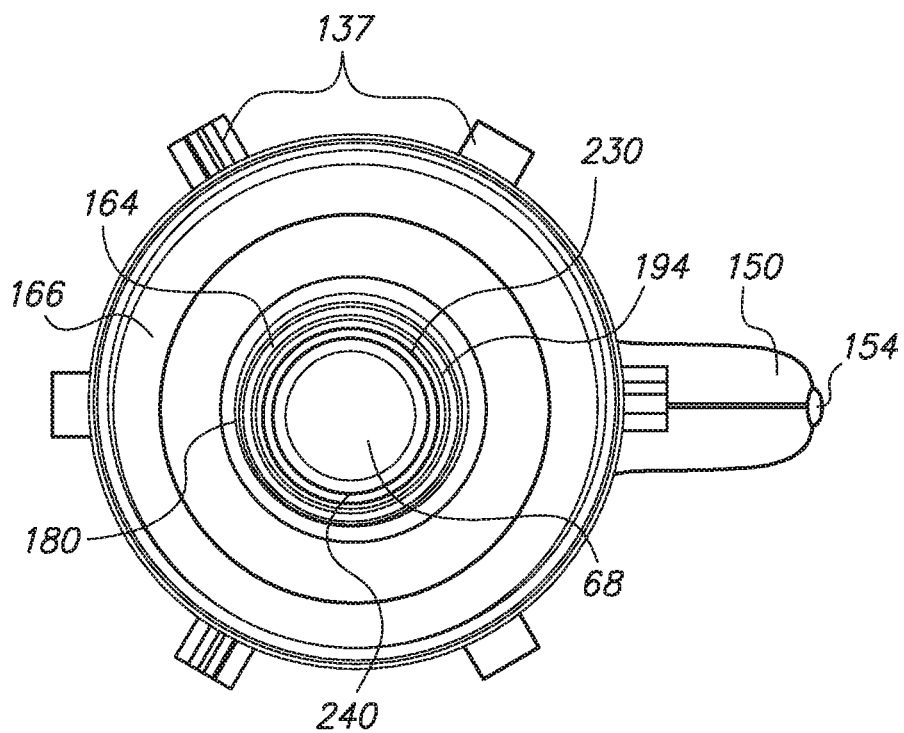
FIGS. 10A-10L illustrate aspects of a patient interface embodiment that features a fidicial configuration selected to assist with in-situ eye orientation determination.
Figure 10B:
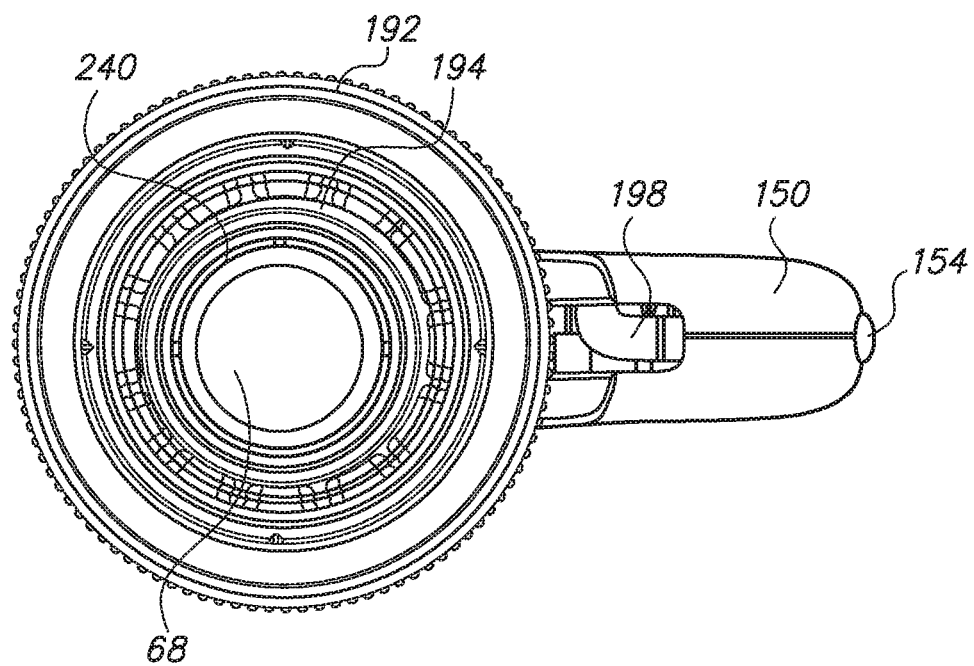
Figure 10C:
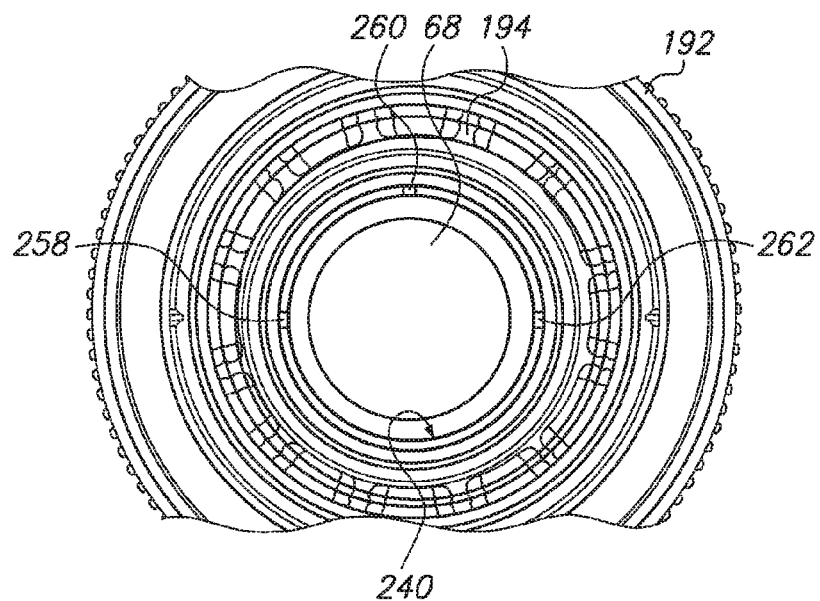
Figure 10D:
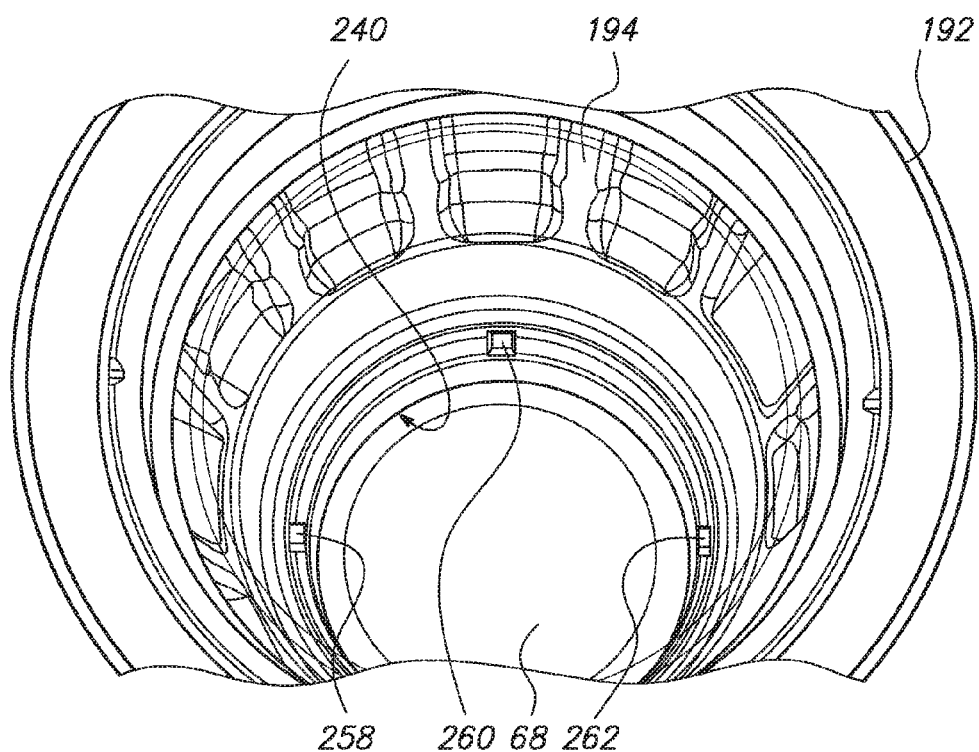
Figure 10E:
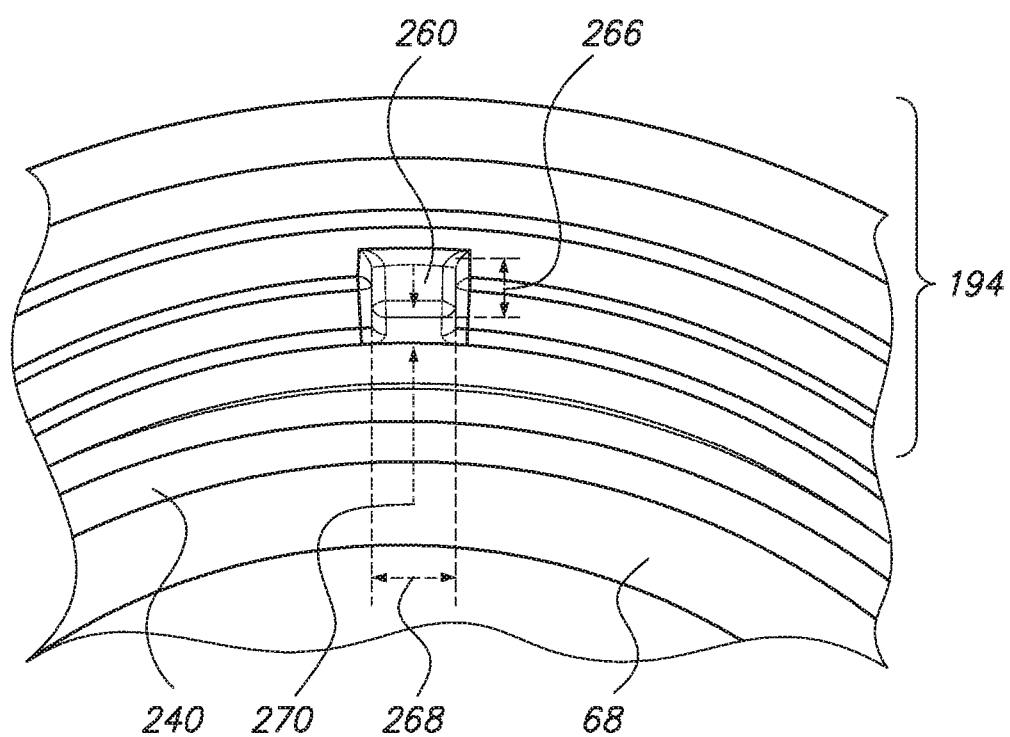

Referring to FIG. 10A, with a patient interface assembly intercoupled between an eye of a patient (68) and an interventional system such as that (2) shown in FIG. 1, the imaging subsystem may be configured to have a field of view directed through the aperture (180, 230) of the patient interface housing (166, 164), across the lens element (not shown in FIG. 10A; see element 92 of FIGS. 5B and 5C, for example), through any associated fluid (not shown in FIG. 10A; see element 172 of FIGS. 5B and 5C, for example), to the surface of the eye (68) and into the eye. FIG. 10B shows a similar view with the top portion of the patient interface housing (166) removed. FIG. 10C shows a closer view with arrows pointing out the location of the inner seal (240) relative to the eye (68), and also the locations of three fiducial markers (258, 260, 262) that are coupled to, defined by, or formed within the lower frustoconical portion (194) of the patient interface housing. FIG. 10D shows another view at a different orientation, and FIG. 10E shows a close-up view of one of the fiducial features (260), which in this embodiment represents a prominent step that has X (266), Y (268), and Z (270) dimensions that are configured to be easily picked up by the associated imaging system. For example, in a configuration featuring an OCT imaging system, dimensions of X and Y that are about 1 mm, and Z that is about mm provide for a fidicial that are easily detectable by the imaging system. As described below in reference to FIG. 11, eye orientation relative to the interventional system based upon an astigmatic or other predetermined axis may be determined intraoperatively if two or more fiducials on the patient interface are placed into some predetermined orientation relative to the preoperatively created marks that are associated with the astigmatic or other predetermined axis. Thus a requisite element of such intraoperative feature set is one or more fiducials coupled to or resident on the patient interface that are within the field of view or detection by the imaging subsystem. FIGS. 10E-10L illustrate several variations.

Figure 10F:
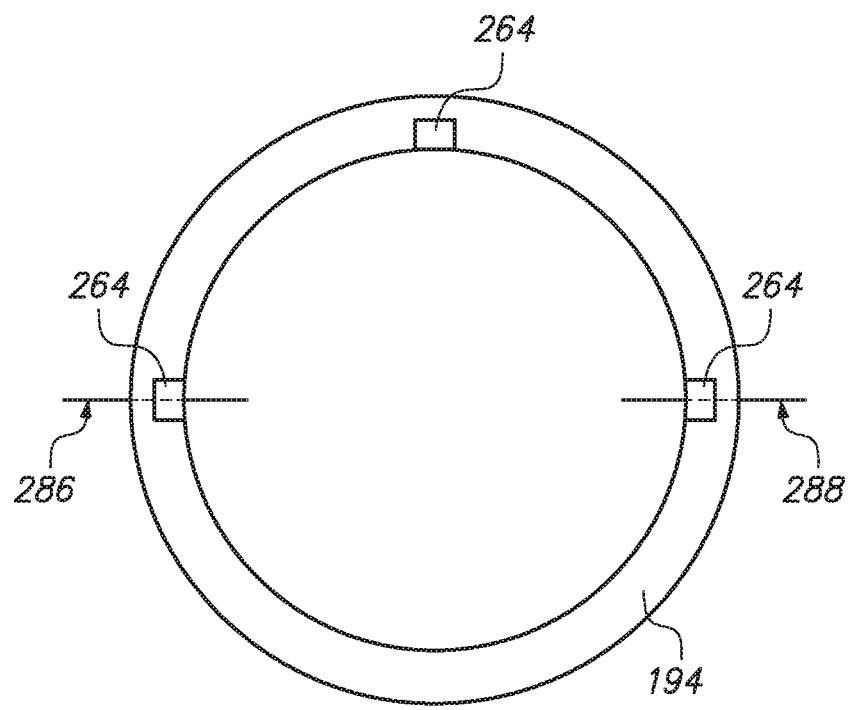
Figure 10G:
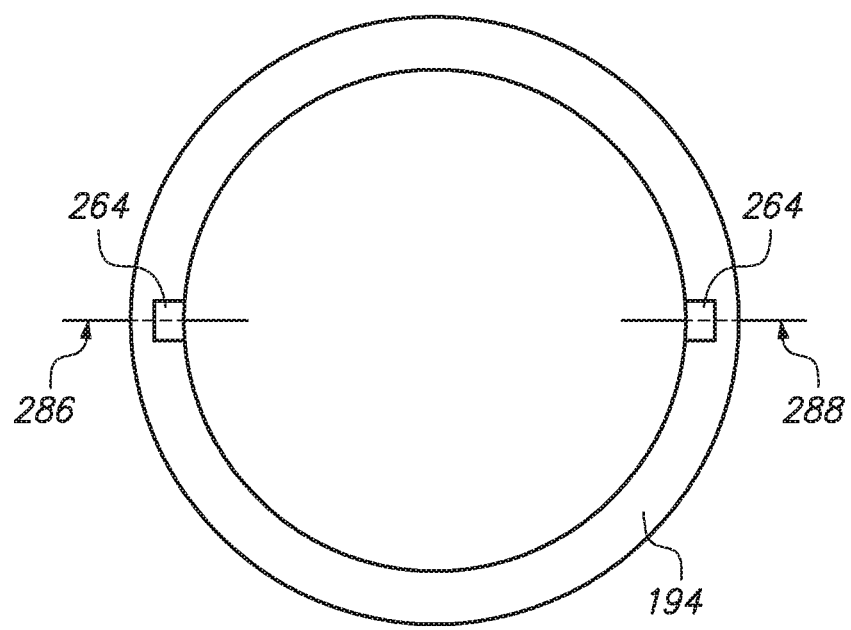

Referring to FIG. 10F, a diagrammatic representation of an inner annulus formed by the distal end of a lower patient interface portion (194) is depicted with a plurality of prominent step fiducials (264) associated therewith, as in the embodiment of FIG. 10C, for example. Two of these fiducials (264) may be manually lined up with the marks (286, 288) that have been manually created preoperatively on the surface of the eye (for example, using a marking pen). One of the challenges is that marks created with marking pens tend to be washed away by the activity of the eye, eyelid, and tears/saline, and thus it is valuable to utilize them to "register" the position and/or orientation of the patient interface relative to the anatomy of the eye, and temporarily fix this relationship with the vacuum or other means, before too much time has elapsed after the time that the marks are created (i.e., before the marks have become too washed away or diffuse to see precisely). Typically the patient care provider will not only want to understand the orientation of the eye relative to the distal system portions (element 160 of FIG. 2C, for example), but will also want to have a geometric axis of the eye substantially aligned with a focal axis of the optical lens housed within the patient interface assembly (typically the focal axis of the optical lens will be aligned to pass through the viewing/treatment aperture of the patient interface housing); indeed, it is desirable to have the geometric axis of the eye directed in a direction approximately parallel to a gravitational force vector when the patient is lying down approximately flat (in other words, have the patient flat and the eye directed "straight up").

In another embodiment, small removable pins or trocar members, such as those commonly used by retinal surgeons and available from suppliers such as the Grieshaber division of Alcon Corporation, may be utilized as markers—or as fiducials themselves—to assist with registering the patient interface to the anatomy from an orientation and/or position perspective. The additional fiducial of the embodiment of FIG. 10F may provide further information regarding which side is "up" from an orientation perspective, but is not absolutely necessary for orientation registration (i.e., two fiducials is functionally adequate for this, as in the embodiment of FIG. 10G, which features two diametrically opposed prominent step fiducials integrated into the lower patient interface portion 194).

Figure 10H:
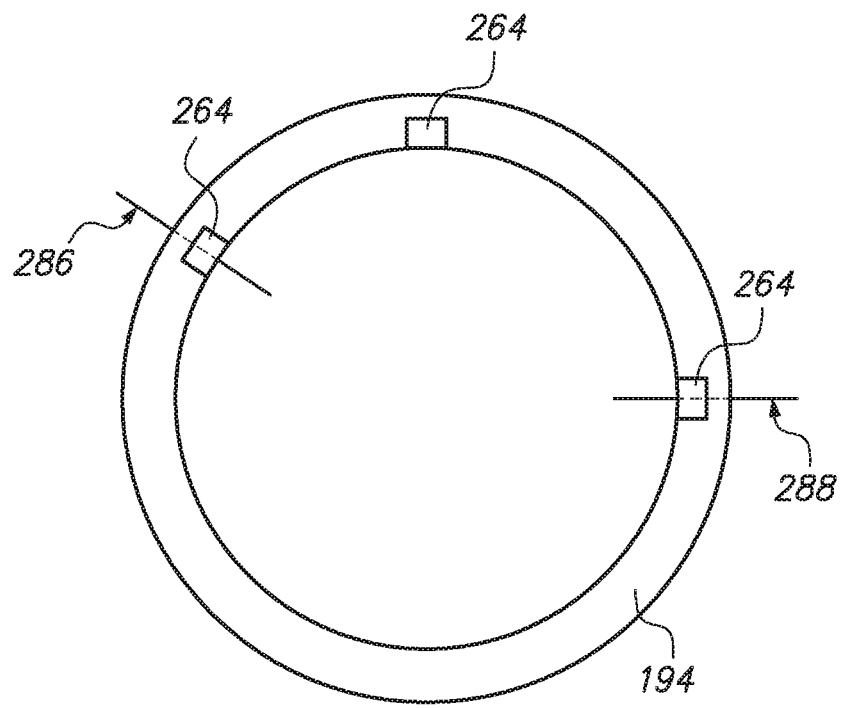

Referring to FIG. 10H, an embodiment is shown to demonstrate that the markers and fiducials need not be lined up in a diametrically opposed configuration, or in any kind of homogeneous pattern relative to each other about the portion of the patient interface exposed to the field of view of the imaging system. The important issue is to understand what the predetermined marks (286, 288) mean, and to line these marks up with the fiducials (264). Although in the depicted embodiment, the fiducials (264) are configured to be directly aligned with the marks (286, 288), in other embodiments these may be misaligned intentionally by a known offset, etc. Again, the key is to make sure that the predetermined information regarding astigmatic axis, etc, that is memorialized in the marks gets transferred to the in-situ surgical scenario in terms of the registration of the patient interface to the anatomy. In other words, if you know what you want to do based upon a preoperative surgical plan and some marks related thereto, you want to make sure that this information can be transferred to the in-situ scenario and utilized understanding where the diagnostic and interventional system is relative to the actual anatomy.

Figure 10I:
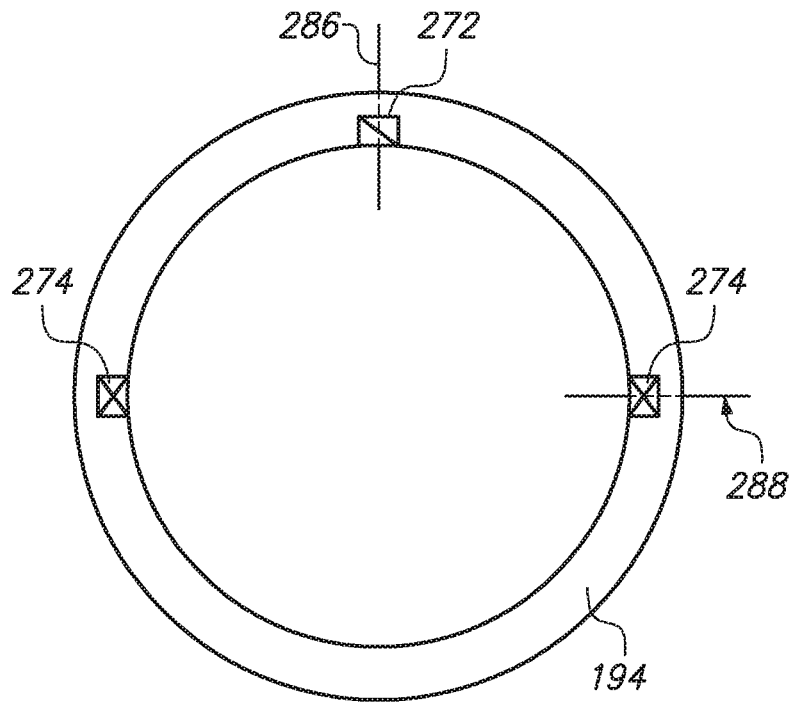
Figure 10J:
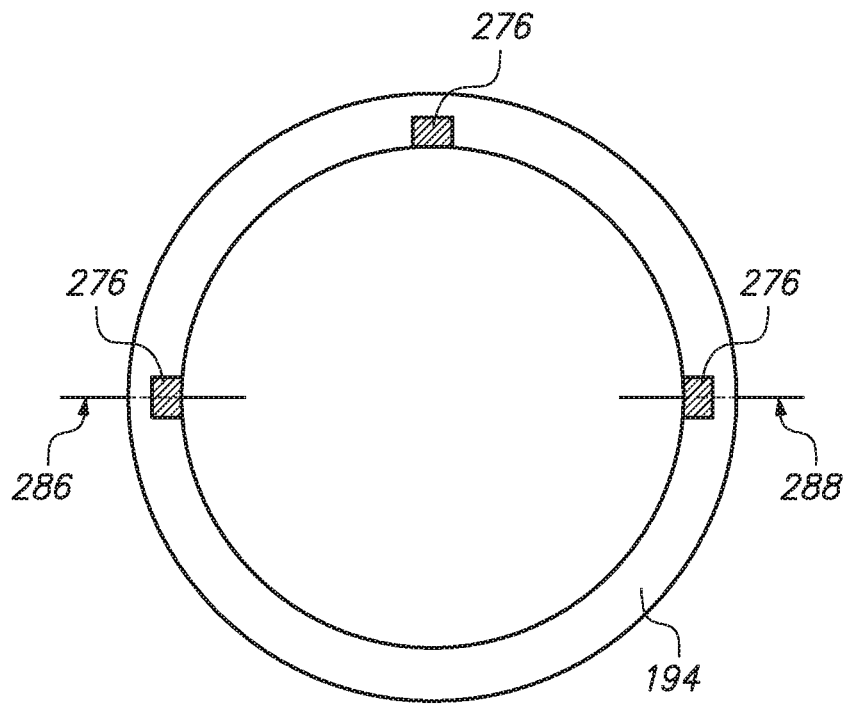
Figure 10K:
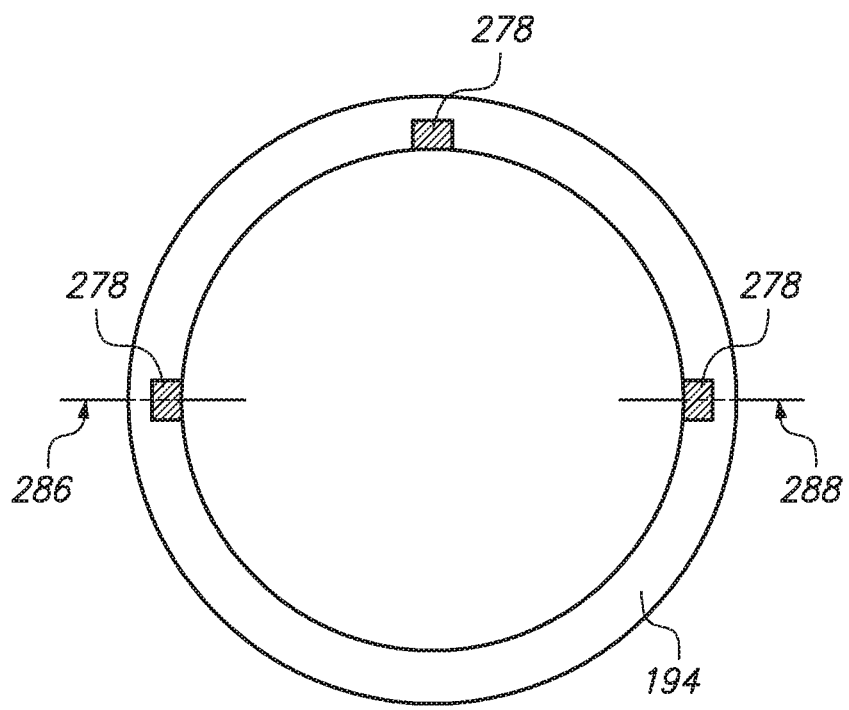
Figure 10L:
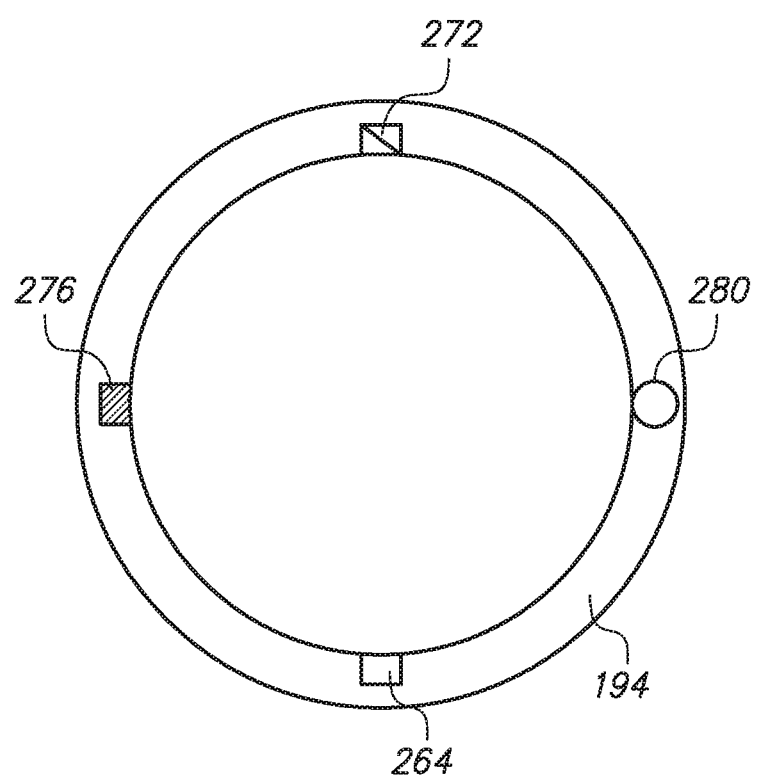

Referring to FIG. 10I, the fiducials need not be prominent steps, as shown in the aforementioned embodiments; they may be depressed steps (i.e., depressed into the surrounding surface of the patient interface), be formed to include prominent or depressed edges (272), or they may comprise contrasting patterns viewable by photography, video, or infrared imaging, for example, as in the "X" pattern visual fiducials (274) of FIG. 10I. FIG. 10J depicts an embodiment with a plurality of high-contrast visual fiducials (276), which may, for example, be black painted portions against a white background as shown, white painted portions against a black background, or the like. Further, the fiducials may comprise a material, such as a fluorescing paint or other fluorescing material, which becomes highly visible in contrast to the surrounding material when illuminated with the appropriate radiation and viewed with the appropriate imaging device (for example, certain carbon tetrachloride solutions fluoresce under infrared radiation and may be imaged with an infrared camera or videocamera). FIG. 10K illustrates an embodiment with fluorescing fiducials (278). Further, the geometry of the fiducials need not be rectangular, square, or edged—it may be any geometry that may be easily detected with the particular imaging system at hand, and different types may be mixed and matched for a particular implementation. The embodiment of FIG. 10L has four different types of fiducials—an edge fiducial (272—may be prominent or depressed relative to the surrounding surface), a hemispherical fiducial (may be prominent or depressed {i.e., concave or convex} relative to the surrounding surface), a contrast fiducial (276), and a step fiducial (may be prominent or depressed relative to the surrounding surface). Thus the one or more fiducials may comprise surface irregularities relative to other surrounding surfaces, and/or highly visible or detectable features or materials.

Figure 11:
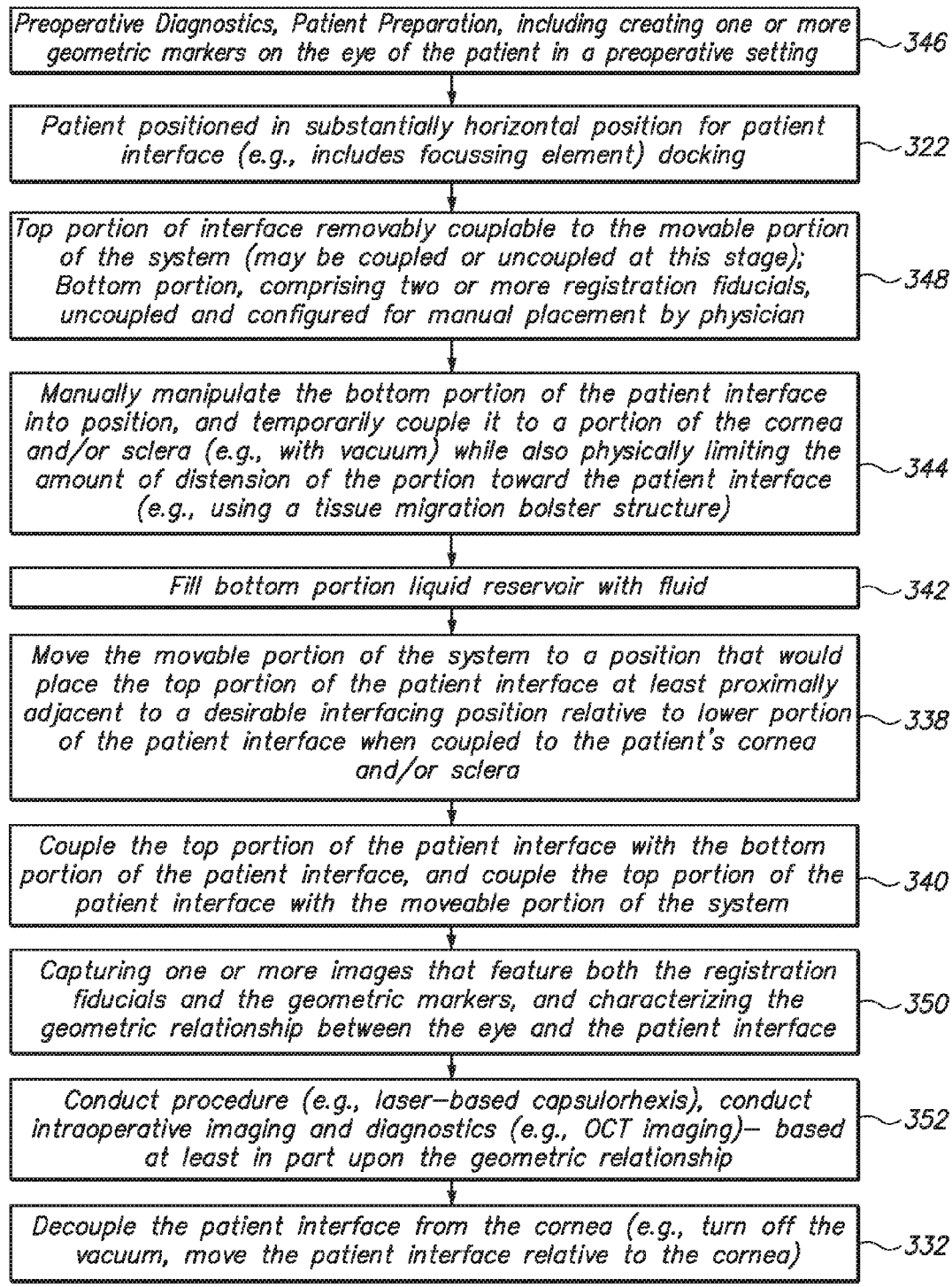
FIG. 11 illustrates aspects of a technique for utilizing configurations such as those described in reference to FIGS. 10A-10L.

Referring to FIG. 11, an implementation utilizing aspects of configurations such as those described in reference to FIGS. 10A-10L is illustrated. As shown in FIG. 11, subsequent to preoperative diagnostics and patient preparation steps, including creating one or more geometric marks on the eye (346), a patient may be positioned in a substantially horizontal position for patient interface docking (322) (i.e., due to the desire to not fight gravity when using a one or two part embodiment; further, in a liquid interface two part embodiment, it is desirable to not have the liquid spill out of the bottom portion). The top portion of the patient interface may be coupled to a movable portion of the system while the bottom portion, containing or comprising two or more fiducials, may remain uncoupled for ease of manual manipulation (348). The lower portion of the patient interface may be removably coupled to the cornea and/or sclera, and this coupling may be enforced with a vacuum load, while a mechanical feature of the lower portion of the patient interface physically limits the amount of distension of the immediately associated portion of the eye toward the patient interface (344). With the docking completed, in a two part liquid configuration, fluid may be added to the bottom portion of the patient interface housing to place the surface of the eye within fluid connection to the lens element coupled to the inside of the bottom portion of the patient interface housing (342). The movable portion of the system may be utilized to move (338) the top portion of the patient interface into a position wherein the top and bottom portions of the patient interface may be intercoupled (the junction being enforced, for example, with another vacuum load) (340). The procedure may be conducted along with intraoperative imaging using systems such as OCT, infrared, light photography, light video, infrared photography or video, ultrasound, Scheimpflug, and the like to not only image the subject tissue structures of the eye, but also to track the positions of the fiducials such that the anatomical positioning relative to the imaging device may be understood (350). After completing the procedure based at least in part upon the geometric relationship between the fiducials and geometric markers (352), the patient interface may be decoupled (i.e., by releasing the vacuum) from the cornea and/or sclera (332). While the embodiment of FIG. 11 combines aspects of the distension-preventing technology described in reference to FIGS. 7A-9, the two-part liquid patient interface configuration of FIGS. 5A-5C, and the marker-fiducial configurations of FIGS. 10A-10L, it is important to emphasize that these aspects need not all be combined in every embodiment of the invention. For example, in one embodiment, a one-piece or two-piece non-liquid patient interface configuration may be augmented with a distention preventing sealing interface without the configurations for using markers and fiducials to register the anatomy to the imaging system; in another embodiment, for example, a two part liquid patient interface configuration may comprise the marker-fiducial features for anatomic registration without the distention preventing sealing interface. The technology features may be used together in various combinations and permutations within the scope of the invention.

Figure 12:
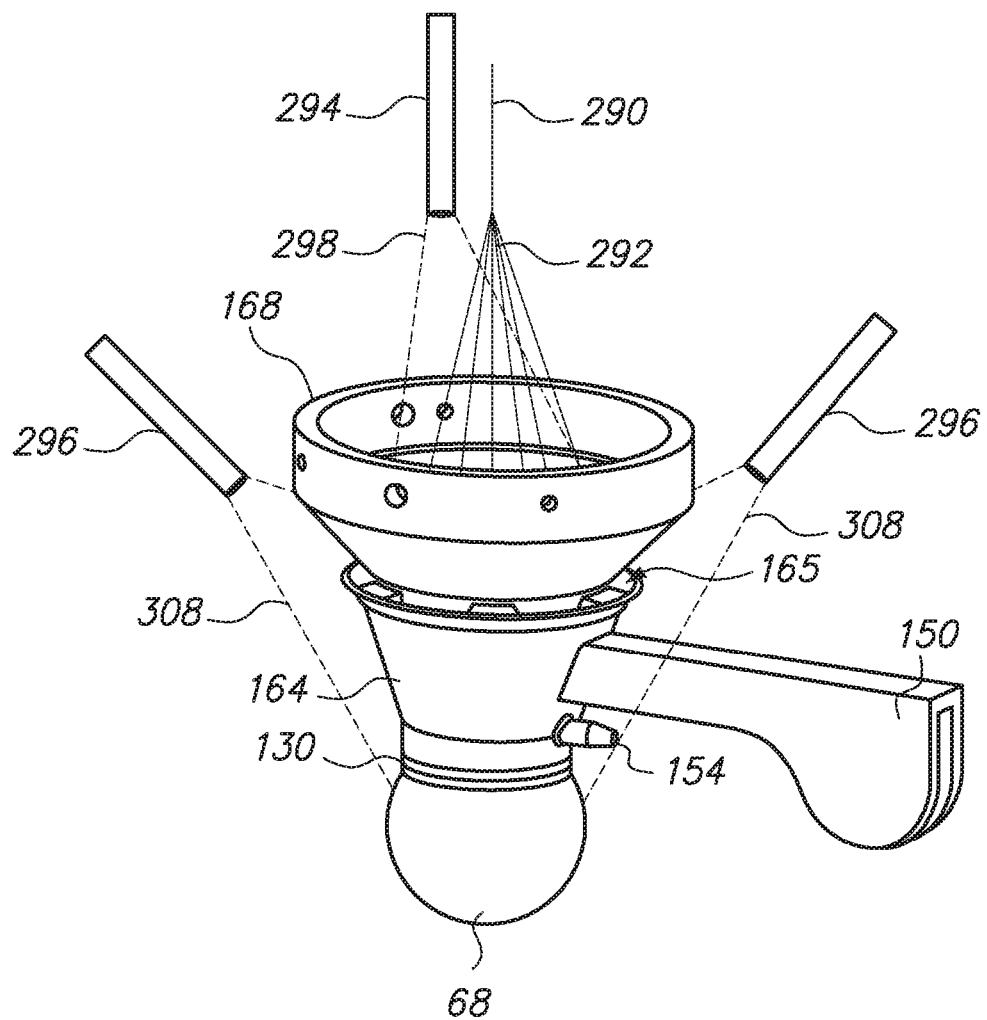
FIG. 12 illustrates aspects of a patient interface configuration having various illumination sources associated therewith.

Referring to FIG. 12, an embodiment similar to that shown in FIG. 5A is depicted, with the exception that several illumination source (296, 294) options are illustrated. As described above in reference to FIG. 1, various types of light sources are suitable for assisting with image and video capture of the subject tissue structures using, for example, conventional camera and video sensors and/or infrared camera and video sensors. Referring again to FIG. 12, in one embodiment, an illumination source (294) will be configured to broadcast illumination radiation in a field (298) configuration whereby the illumination radiation is passed through the central aperture or passageway of the patient interface assembly (168, 164), including through any lens element that may be coupled thereto and positioned across the central aperture, to reach substantially the entire surface of the eye (68) of the patient that is accessible through the patient interface (i.e., the portion of the cornea and/or sclera that is bounded by the inner seal of the engagement assembly 130). In another configuration, also illustrated in FIG. 12, one or more illumination sources (296) may be configured to broadcast illumination radiation in a field (308) configuration whereby the illumination radiation is passed through at least a portion of the patient interface housing assembly (164, 168) to reach substantially the entire surface of the eye (68) of the patient that is accessible through the patient interface (i.e., the portion of the cornea and/or sclera that is bounded by the inner seal of the engagement assembly 130); with such a configuration, depending upon the wavelength of transmitted illumination irradiation, it may be desirable to have one or more portions of the patient interface assembly (164, 168) comprise substantially translucent materials that are selected to pass the illumination irradiation across walls and features of such structures and in toward the subject surface of the eye (68). FIG. 12 also shows an OCT irradiation and/or scatter/reflection beam (290) being passed through the central aperture of the patient interface housing (164, 168), and a diagrammatic representation of a scanning/broadcast and scatter/reflection field (292) for this imaging technology, the field (292) being akin to a field of view for such technology. The desired field of view of the OCT imaging system preferably includes as much of the subject eye (68) tissue as possible given the position of the OCT source and the surface of the eye (68) of the patient that is accessible through the patient interface (i.e., the portion of the cornea and/or sclera that is bounded by the inner seal of the engagement assembly 130; the OCT may also be able to provide additional data by imaging "through" one or more elements of the patient interface assembly, such as through the inner seal 240 as engaged with the eye 68), and, as described above, the OCT may function as a 3-dimensional sensor for monitoring positions of fiducials which may be coupled to, or formed in, portions of the patient interface assembly. For example, as described above, the OCT or other imaging sensor may be configured to capture one or more images that feature both the registration fiducials coupled to or formed within the patient interface and the geometric markers which may be placed or created preoperatively (i.e., with a marker, small removable trocar, etc), and when the patient interface is engaged with the eye intraoperatively, the geometric relationship between the anatomy of the eye (based upon the geometric markers) and the imaging device may be accurately characterized when the geometric relationship between the patient interface and the geometric markers is known (i.e., by virtue of lining the markers up with the fiducials in some quantifiable way). In other words, with such a configuration, the preoperatively created geometric markers, based upon healthcare provider analysis of the patient's anatomy, establish an axis or other geometric landmark which may be mapped to the patient interface in-situ by lining the geometric markers up with the fiducials of the patient interface; then with an imaging device configured to capture images of both the anatomy and the fiducials together, the geometric relationship between the anatomy and the imaging device may be determined or characterized with geometric transformation. In a configuration wherein a two-dimensional imaging device is utilized, such as a conventional camera or video system using visible or infrared light, an assumption may be made that the fiducials of the patient interface are substantially co-planar (and, indeed, the fiducials may be specifically configured to be substantially co-planar), and the quantitative analysis may lead to characterizations of positions and/or movements of the fiducials and associated eye anatomy relative to a plane that is substantially perpendicular to the axis of the aperture of the patient interface through which the imaging device is operated. In an embodiment wherein the imaging device comprises an OCT device, additional information may be derived, since OCT is capable of measuring fully three-dimensional positions of the various structures of interest, such as each of the fiducials and various anatomical features of the eye (68). In other words, the three-dimensional capability of the OCT technology works as a depth sensor as well as a position sensor. Although we specifically describe OCT in this scenario, it is to be understood that all of the 3-dimensional imaging modalities described herein may be utilized to provide 3-dimensional position sensing. Thus, in an embodiment wherein OCT is utilized to characterize the geometric relationship of the fiducials, the imaging device, and the anatomy, the three dimensional motion of the patient interface may be characterized in pitch, yaw, and roll as well as X, Y, and Z given updated three-dimensional position data regarding each of the fiducials. Such calculated information may be utilized to characterize the eye anatomy to which the patient interface may be intercoupled—or may be utilized to successfully dock/engage the patient interface with the surface of the eye before temporarily vacuum locking the two together as described above (in other words, the pitch, yaw, roll, x, y, z data for the patient interface may be utilized to ensure that the patient interface is being engaged against the eye in a preferred orientation that is not "cockeyed" relative to the surface of the eye upon engagement, etc). Positional information derived from image or signal analysis of the image(s) or detection(s) of the patient interface as it is being brought into contact with the system via IO (302) and control electronics (300) may be employed to provide guidance to the user. This guidance may in the form of a visible cue or marker displayed upon GUI (304) that is intended for the user to recognize and manually compensate for using IO (306) to position the patient via UI (306) to control motion control system (70), or similar means. The abovementioned positional information may also be used to generate signals that can be utilized by control electronics (300) directly to control motion control system (70) in order to automatically and accurately couple the patient to the system. Information about the axial position of the patient interface, or the system member to which it is attached may further be used to judge the depth location of the patient when using en-face 2-dimensional imaging means such as infrared, light photography, light video, and/or infrared photography or video.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A method for ophthalmic intervention on an eye of a patient, comprising:
   a. orienting a field of view of an imaging device toward the eye of the patient;
   b. coupling a distal end of a patient interface housing to one or more seals configured to be directly engaged with one or more surfaces of the eye of the patient, and coupling a proximal end of the patient interface housing to a patient workstation such that at least a portion of the field of view of the imaging device passes through a passage of the patient housing defined by the proximal and distal ends;
   c. imaging, within the field of the view of the imaging device, three or more registration fiducials, which include first and second registration fiducials coupled to the patient interface housing in a predetermined geometric configuration relative to the patient interface housing in reference to predetermined geometric markers on the eye of the patient, which are also imaged by the imaging device; and
   d. processing imaging data generated via the imaging device so as to determine an angular orientation of the eye relative to the patient interface based on the first and second fiducial and the predetermined geometric markers and also to determine an up or down orientation of the patient interface housing relative to the eye based on the location of a third fiducial.

2. The method of claim 1, wherein a laser system is operatively coupled to the imaging device.

3. The method of claim 2, further comprising producing a treatment beam with the laser system that may be directed through the passage of the patient interface housing and into the eye of the patient.

4. The method of claim 3, wherein the treatment beam is suitable for creating dielectric breakdown within a cataractous crystalline lens of the eye.

5. The method of claim 4, wherein the treatment beam is a pulsed treatment beam with a pulse repetition rate between about 1 kHz and about 200 kHz.

6. The method of claim 4, wherein the treatment beam has a wavelength between about 800 nm and about 1,100 nm.

7. The method of claim 4, wherein the treatment beam is a pulsed treatment beam having a pulse energy between about 1 microjoule and about 1,000 microjoules.

8. The method of claim 4, wherein the treatment beam is a pulsed treatment beam with a pulse duration between about 100 femtoseconds and about 10 picoseconds.

9. The method of claim 1, wherein the patient interface housing comprises an optical lens coupled to the housing having a focal axis aligned to pass through the passage of the housing.

10. The method of claim 1, further comprising directing illumination radiation from a position adjacent the imaging device toward the eye of the patient.

11. The method of claim 1, wherein at least a portion of the illumination radiation is directed through the passage of the patient interface housing.

12. The method of claim 1, wherein at least a portion of the patient interface housing is translucent to the illumination radiation, and at least a portion of the illumination radiation is directed across the translucent portion of the patient interface housing toward the eye of the patient.

13. The method of claim 10, wherein the illumination radiation is infrared radiation.

14. The method of claim 10, wherein the illumination radiation is visible light radiation.

15. The method of claim 1, wherein the imaging device comprises an optical coherence tomography system configured to measure the coherence of radiation scattered into an interferometer from the field of view.

16. The method of claim 13, wherein the fiducials comprise one or more materials that fluoresce in infrared radiation.

17. The method of claim 13, wherein the fiducials comprise one or more materials that highly contrast in infrared radiation relative to other surrounding materials.

18. The method of claim 13, wherein the fiducials comprise one or more surface irregularities relative to other surrounding surfaces.

19. The method of claim 18, wherein the one or more surface irregularities are selected from the group consisting of: a concave feature, a convex feature, a depressed edge, a depressed step, a projecting edge, a projecting step, and an intersection of lines.

20. The method of claim 14, wherein the fiducials comprise one or more materials that highly contrast in visible light radiation relative to other surrounding materials.

21. The method of claim 14, wherein the fiducials comprise one or more surface irregularities relative to other surrounding surfaces.

22. The method of claim 21, wherein the one or more surface irregularities are selected from the group consisting of: a concave feature, a convex feature, a depressed edge, a depressed step, a projecting edge, a projecting step, and an intersection of lines.

23. The method of claim 15, wherein the fiducials comprise one or more surface irregularities relative to other surrounding surfaces.

24. The method of claim 23, wherein the one or more surface irregularities are selected from the group consisting of: a concave feature, a convex feature, a depressed edge, a depressed step, a projecting edge, a projecting step, and an intersection of lines.

25. The method of claim 1, wherein the three or more fiducials are positioned upon an inner annulus formed by the distal end of the patient interface housing.

26. The method of claim 25, wherein the first and second fiducials are positioned at opposite sides of the inner annulus.

27. The method of claim 25, wherein the three or more fiducials comprise three fiducials distributed nonhomogeneously about the inner annulus.

* * * * *